(12) United States Patent
Lee et al.

(10) Patent No.: US 8,409,175 B2
(45) Date of Patent: Apr. 2, 2013

(54) SURGICAL INSTRUMENT GUIDE DEVICE

(76) Inventors: Woojin Lee, Hopkinton, MA (US);
Andres Chamorro, Waltham, MA (US)

( * ) Notice: Subject to any disclaimer, the term of this patent is extended or adjusted under 35 U.S.C. 154(b) by 961 days.

(21) Appl. No.: 12/387,717

(22) Filed: May 6, 2009

(65) Prior Publication Data
US 2009/0299344 A1  Dec. 3, 2009

Related U.S. Application Data

(63) Continuation-in-part of application No. 11/242,642, filed on Oct. 3, 2005, now Pat. No. 7,842,028.

(60) Provisional application No. 60/700,776, filed on Jul. 20, 2005.

(51) Int. Cl.
*A61B 1/01* (2006.01)

(52) U.S. Cl. ............ 606/1; 600/114; 600/137; 600/141; 600/142; 600/146; 600/149

(58) Field of Classification Search .................. 600/114, 600/137, 141, 142, 146, 149; 606/1
See application file for complete search history.

(56) References Cited

U.S. PATENT DOCUMENTS

| | | |
|---|---|---|
| 2,028,635 A | 1/1936 | Wappler |
| 2,507,710 A | 5/1950 | Grosso |
| 2,790,437 A | 4/1957 | Moore |
| 3,557,780 A | 1/1971 | Sato |
| 3,858,577 A | 1/1975 | Bass et al. |
| 3,895,636 A | 7/1975 | Schmidt |
| 4,483,562 A | 11/1984 | Schoolman |
| 4,688,554 A | 8/1987 | Habib |
| 4,728,020 A | 3/1988 | Green et al. |
| 4,763,669 A | 8/1988 | Jaeger |
| 4,872,456 A | 10/1989 | Hasson |
| 4,880,015 A | 11/1989 | Nierman |
| 4,944,093 A | 7/1990 | Falk |
| 4,944,741 A | 7/1990 | Hasson |
| 4,945,920 A | 8/1990 | Clossick |
| 5,002,543 A | 3/1991 | Bradshaw et al. |
| 5,042,707 A | 8/1991 | Taheri |
| 5,209,747 A | 5/1993 | Knoepfler |
| 5,271,381 A | 12/1993 | Ailinger et al. |
| 5,273,026 A | 12/1993 | Wilk |
| 5,275,608 A | 1/1994 | Forman et al. |
| 5,314,424 A | 5/1994 | Nicholas |

(Continued)

FOREIGN PATENT DOCUMENTS

| | | |
|---|---|---|
| EP | 0 095 970 A2 | 12/1983 |
| EP | 0 448 284 A2 | 9/1991 |

(Continued)

OTHER PUBLICATIONS

Nakamura et al., Multi-DOF Forceps Manipulator System for Laparoscopic Surgery—Mechanism Miniaturized & Evaluation of New Enterfaces, 5 pgs. Oct. 14-17, 2001.

(Continued)

*Primary Examiner* — Aaron Roane

(57) ABSTRACT

An instrument guide device comprises an elongated guide shaft having proximal and distal ends and including an instrument lumen for receiving therethrough a manually operated instrument having an instrument shaft. A distal bendable member is disposed at the distal end of the guide shaft and a proximal bendable member is disposed at the proximal end of the guide shaft. Actuation means extends between the distal and proximal bendable members and provides a bending of the distal bendable member controlled from the proximal bendable member. The proximal bendable member is controlled from the manually operated instrument to cause a corresponding bending of said distal bendable member. A locking mechanism has locked and unlocked positions and includes a ball and socket arrangement disposed about the proximal bendable member and a cinch member for locking the ball and socket arrangement.

20 Claims, 22 Drawing Sheets

U.S. PATENT DOCUMENTS

| | | | |
|---|---|---|---|
| 5,330,502 A | 7/1994 | Hassler et al. |
| 5,344,428 A | 9/1994 | Griffiths |
| 5,383,880 A | 1/1995 | Hooven |
| 5,386,818 A | 2/1995 | Schneebaum et al. |
| 5,395,367 A | 3/1995 | Wilk |
| 5,405,344 A | 4/1995 | Williamson et al. |
| 5,433,721 A | 7/1995 | Hooven et al. |
| 5,441,494 A | 8/1995 | Ortiz |
| 5,454,827 A | 10/1995 | Aust et al. |
| 5,501,654 A | 3/1996 | Failla et al. |
| 5,520,678 A | 5/1996 | Heckele et al. |
| 5,618,294 A | 4/1997 | Aust et al. |
| 5,643,294 A | 7/1997 | Tovey et al. |
| 5,702,408 A | 12/1997 | Wales et al. |
| 5,759,151 A | 6/1998 | Sturges |
| 5,766,196 A | 6/1998 | Griffiths |
| 5,772,578 A | 6/1998 | Heimberger et al. |
| 5,823,066 A | 10/1998 | Huitema et al. |
| 5,827,177 A | 10/1998 | Oneda et al. |
| 5,851,208 A | 12/1998 | Trott |
| 5,855,569 A | 1/1999 | Komi |
| 5,873,817 A | 2/1999 | Kokish et al. |
| 5,899,425 A | 5/1999 | Corey Jr. et al. |
| 5,899,914 A | 5/1999 | Zirps et al. |
| 5,904,647 A | 5/1999 | Ouchi |
| 5,916,146 A | 6/1999 | Allotta et al. |
| 5,916,147 A | 6/1999 | Boury |
| 5,921,956 A | 7/1999 | Grinberg et al. |
| 5,938,678 A | 8/1999 | Zirps et al. |
| 5,944,713 A | 8/1999 | Schuman |
| 6,126,633 A | 10/2000 | Kaji et al. |
| 6,174,280 B1 | 1/2001 | Oneda et al. |
| 6,210,377 B1 | 4/2001 | Ouchi |
| 6,210,378 B1 | 4/2001 | Ouchi |
| 6,210,416 B1 | 4/2001 | Chu et al. |
| 6,270,453 B1 | 8/2001 | Sakai |
| 6,551,238 B2 | 4/2003 | Staud |
| 6,623,424 B2 | 9/2003 | Hayakawa et al. |
| 6,638,214 B2 | 10/2003 | Akiba |
| 6,656,195 B2 | 12/2003 | Peters et al. |
| 6,666,854 B1 | 12/2003 | Lange |
| 6,669,073 B2 | 12/2003 | Milliman et al. |
| 6,752,756 B2 | 6/2004 | Lunsford et al. |
| 6,755,338 B2 | 6/2004 | Hahnen et al. |
| 6,761,717 B2 | 7/2004 | Bales et al. |
| 7,128,253 B2 | 10/2006 | Mastri et al. |
| 7,147,650 B2 | 12/2006 | Lee |
| 2002/0045803 A1 | 4/2002 | Abe et al. |
| 2002/0095175 A1 | 7/2002 | Brock et al. |
| 2002/0133173 A1 | 9/2002 | Brock et al. |
| 2002/0156497 A1 | 10/2002 | Nagase et al. |
| 2002/0177750 A1 | 11/2002 | Pilvisto |
| 2002/0177847 A1 | 11/2002 | Long |
| 2003/0065359 A1 | 4/2003 | Weller et al. |
| 2003/0109898 A1 | 6/2003 | Schwarz et al. |
| 2003/0135204 A1 | 7/2003 | Lee et al. |
| 2003/0149338 A1 | 8/2003 | Francois et al. |
| 2003/0216618 A1 | 11/2003 | Arai |
| 2004/0049205 A1 | 3/2004 | Lee et al. |
| 2004/0111009 A1 | 6/2004 | Adams et al. |
| 2004/0138529 A1 | 7/2004 | Wiltshire et al. |
| 2004/0176751 A1 | 9/2004 | Weitzner et al. |
| 2004/0193146 A1 | 9/2004 | Lee et al. |
| 2004/0236316 A1 | 11/2004 | Danitz et al. |
| 2005/0049580 A1 | 3/2005 | Brock et al. |
| 2005/0107667 A1 | 5/2005 | Danitz et al. |
| 2005/0228440 A1 | 10/2005 | Brock et al. |
| 2005/0251112 A1 | 11/2005 | Danitz et al. |
| 2005/0273084 A1 | 12/2005 | Hinman et al. |
| 2005/0273085 A1 | 12/2005 | Hinman et al. |
| 2007/0250110 A1 | 10/2007 | Lu et al. |
| 2008/0172086 A1 | 7/2008 | Hillstead et al. |
| 2008/0262538 A1 | 10/2008 | Danitz et al. |
| 2008/0294191 A1 | 11/2008 | Lee |
| 2009/0069842 A1 | 3/2009 | Lee et al. |

FOREIGN PATENT DOCUMENTS

| | | |
|---|---|---|
| EP | 0 626 604 A2 | 5/1994 |
| EP | 0 427 949 B1 | 6/1994 |
| GB | 2 143 920 | 2/1985 |
| WO | WO 90/05491 | 5/1990 |
| WO | WO 92/01414 | 2/1992 |
| WO | WO 94/17965 | 8/1994 |

OTHER PUBLICATIONS

Ryoichi Nakamura et al., Multi-DOF Manipulator System for Laparoscopic Surgery, 8 pgs. Oct. 3, 2004.

Ryoichi Nakamura et al., Development of Forceps Manipulator System for Laparoscopic Surgery, 6 pgs.

Hiromasa Yamashita et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

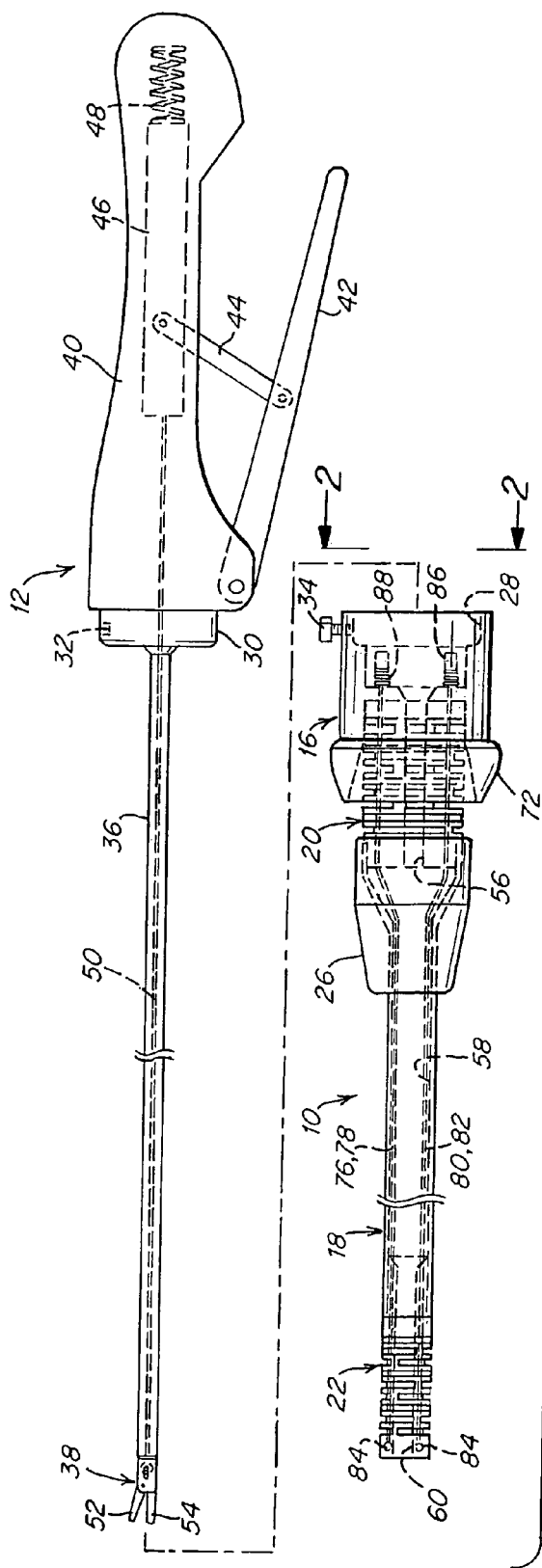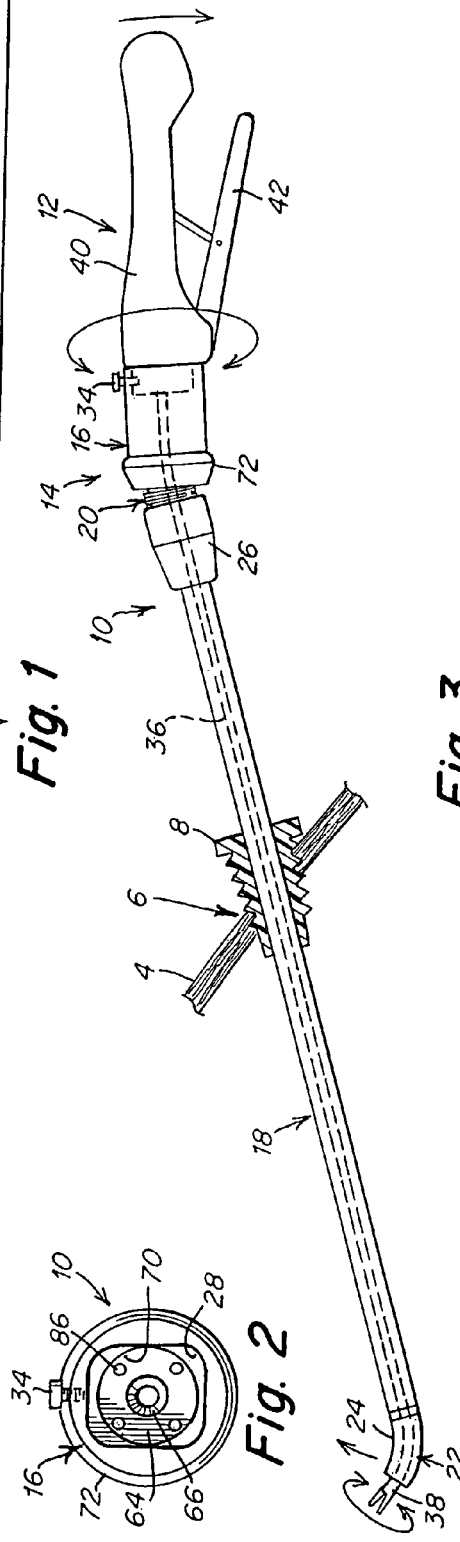

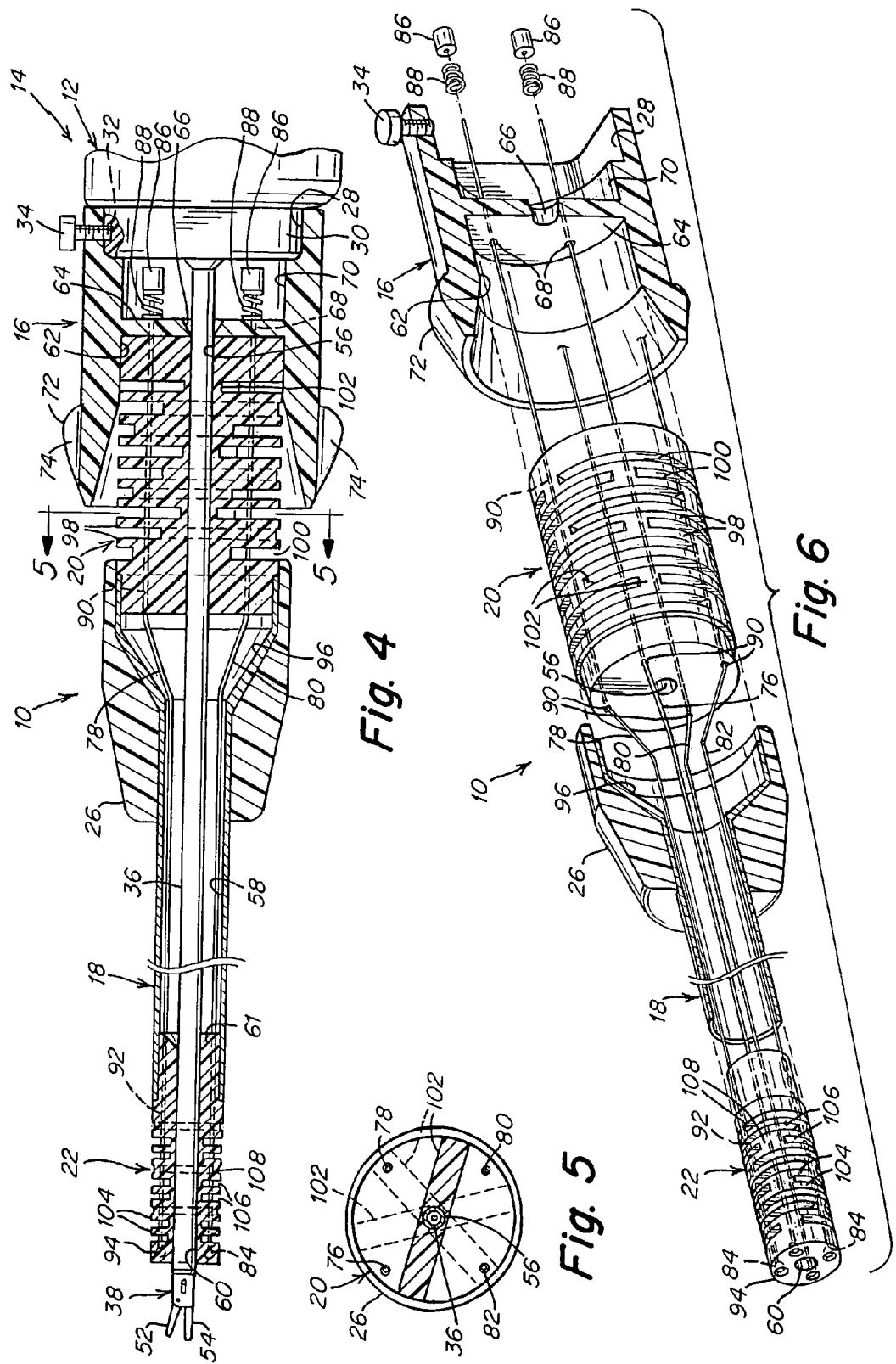

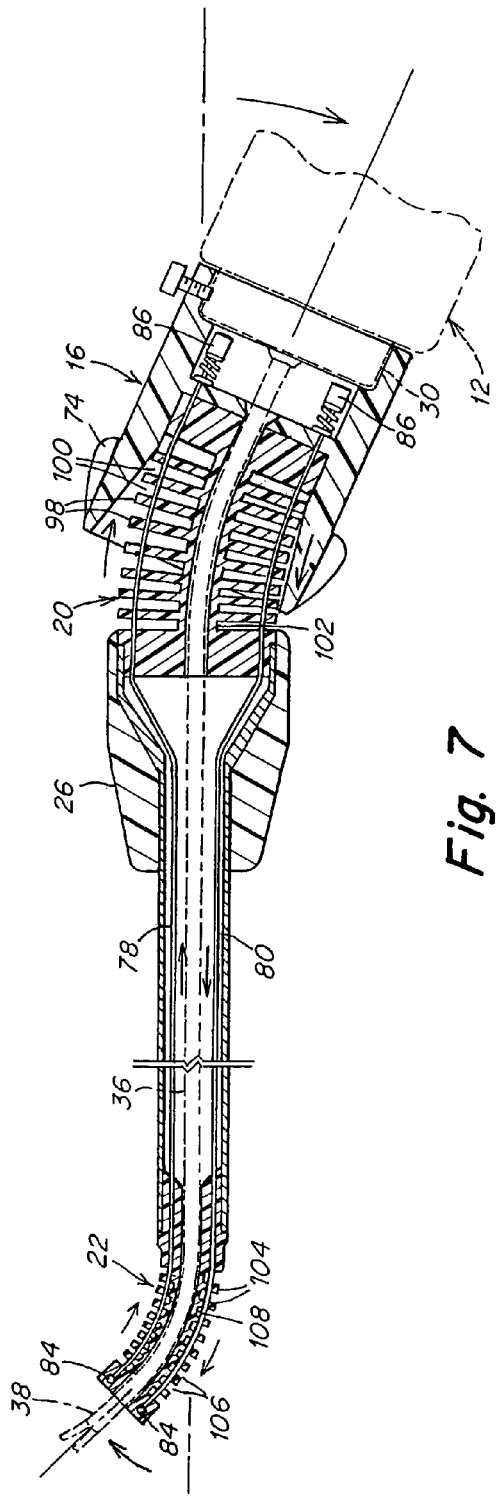
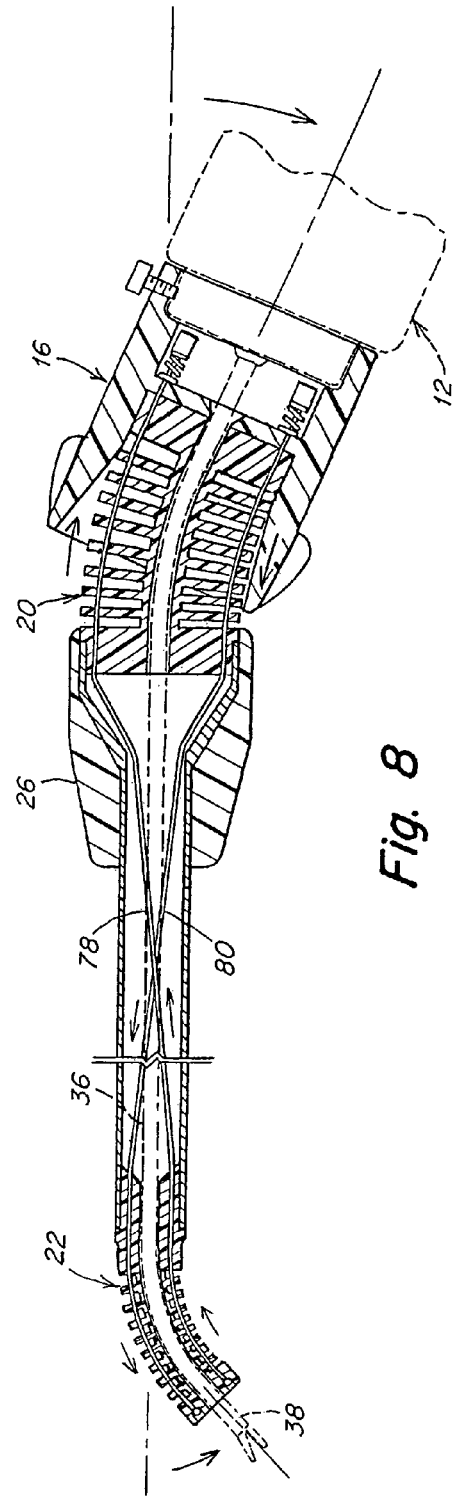
Fig. 7
Fig. 8

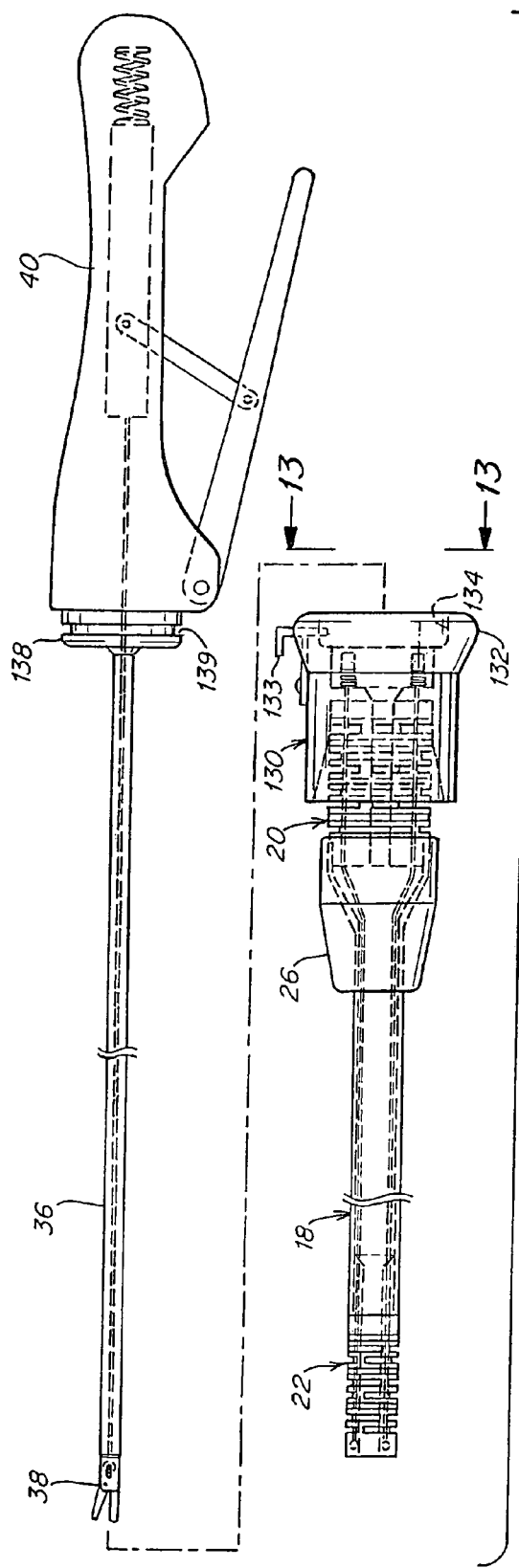
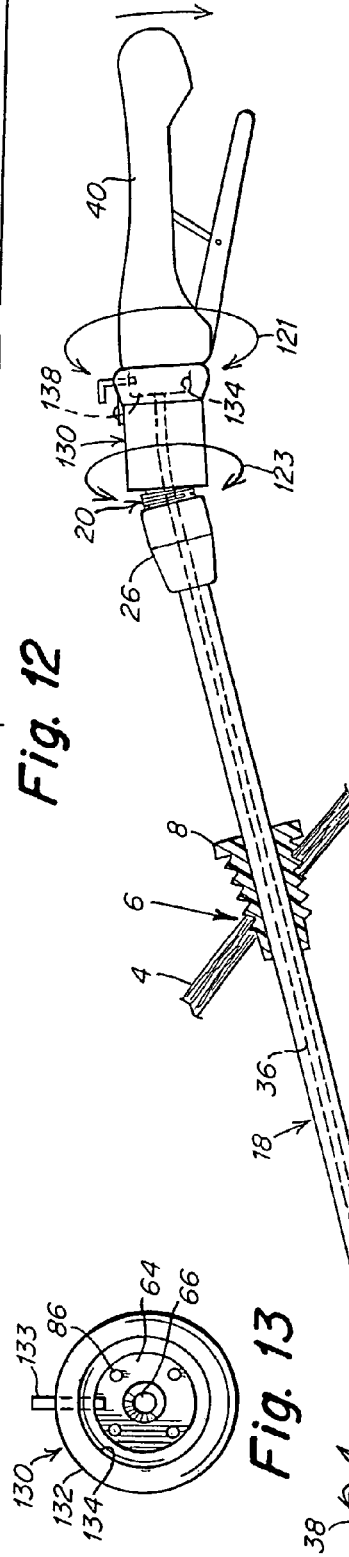
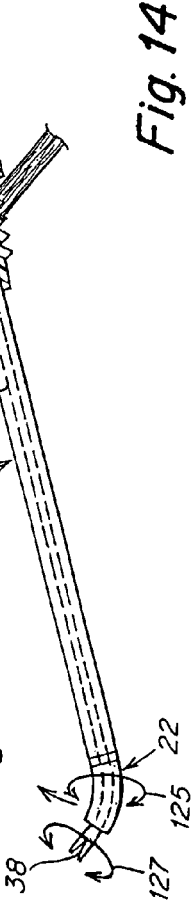
Fig. 12
Fig. 13
Fig. 14

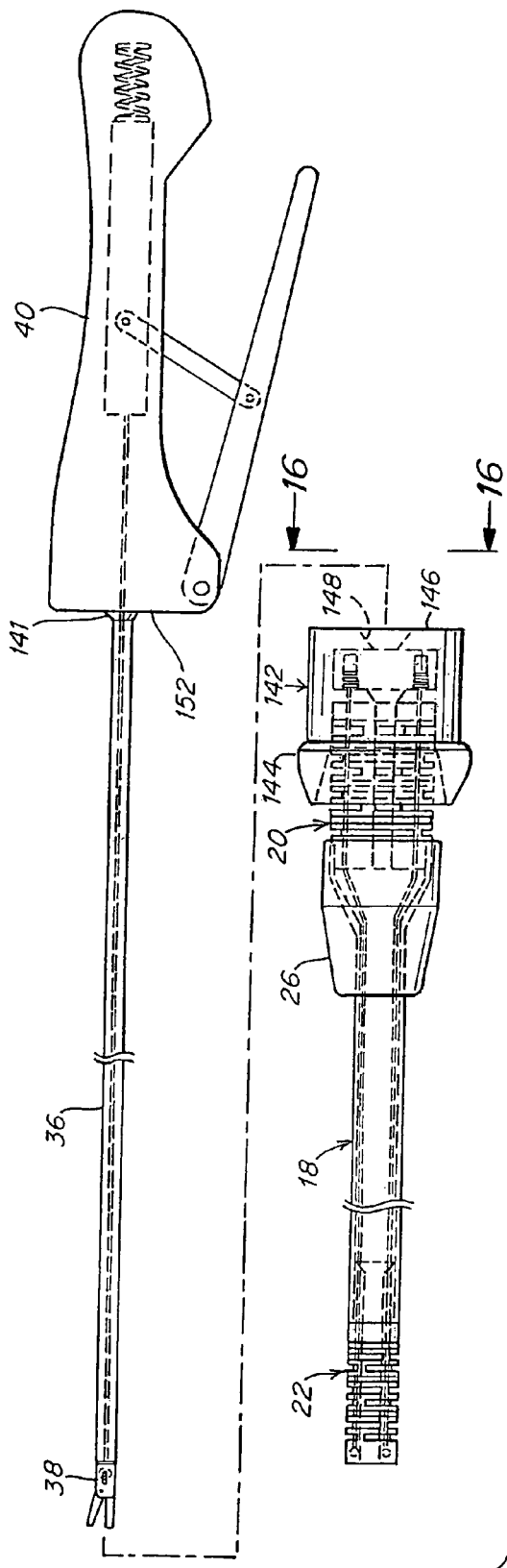
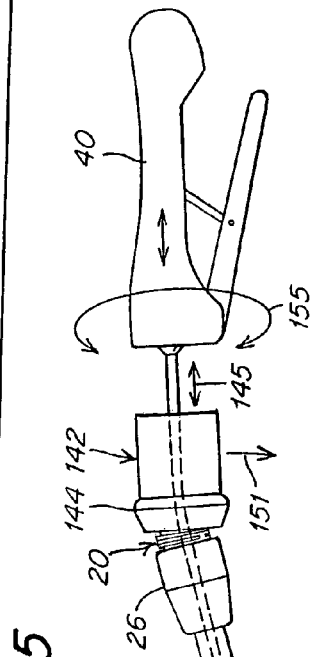
Fig. 15
Fig. 16
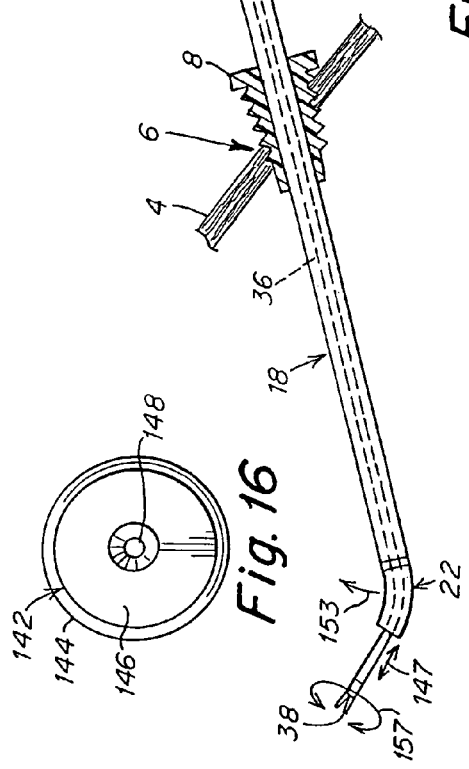
Fig. 17

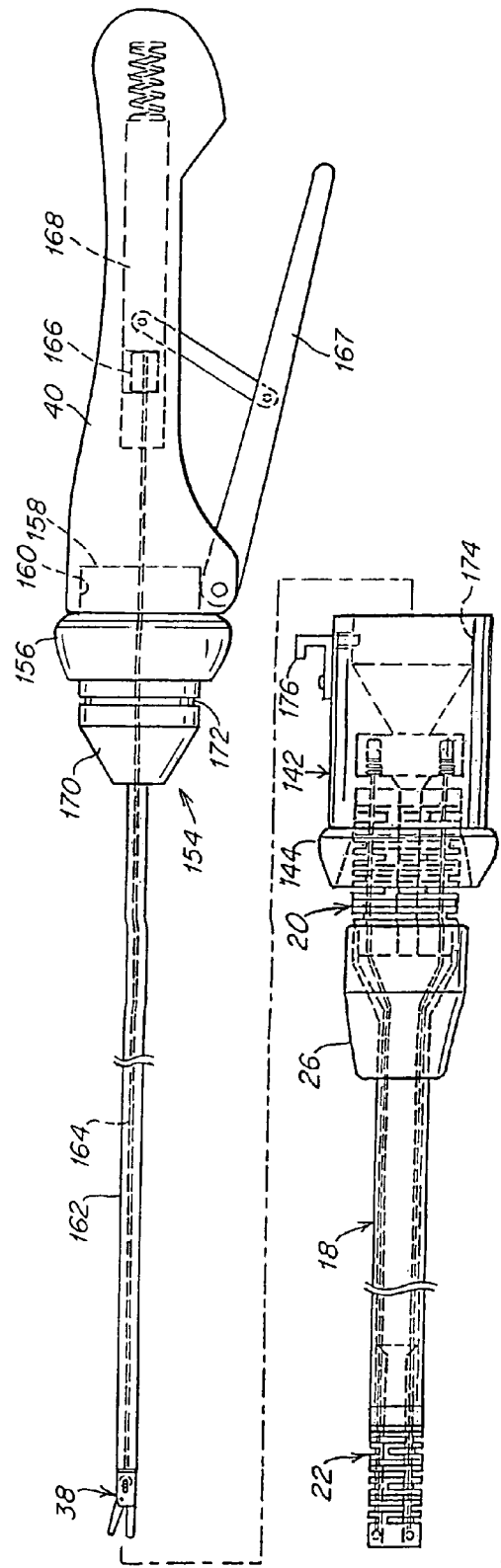
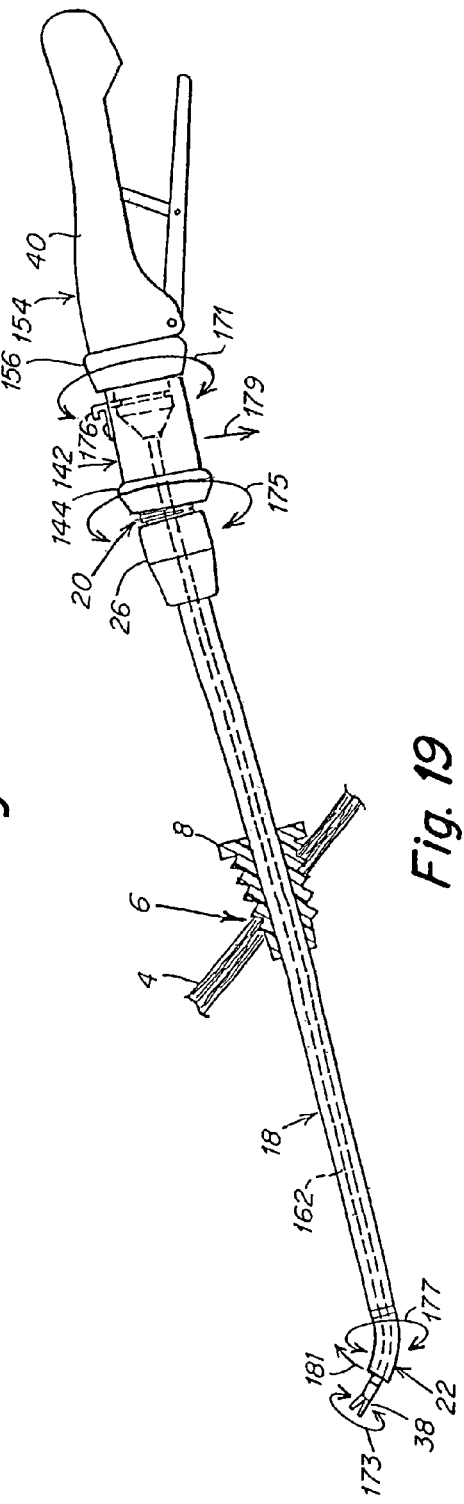
Fig. 18
Fig. 19

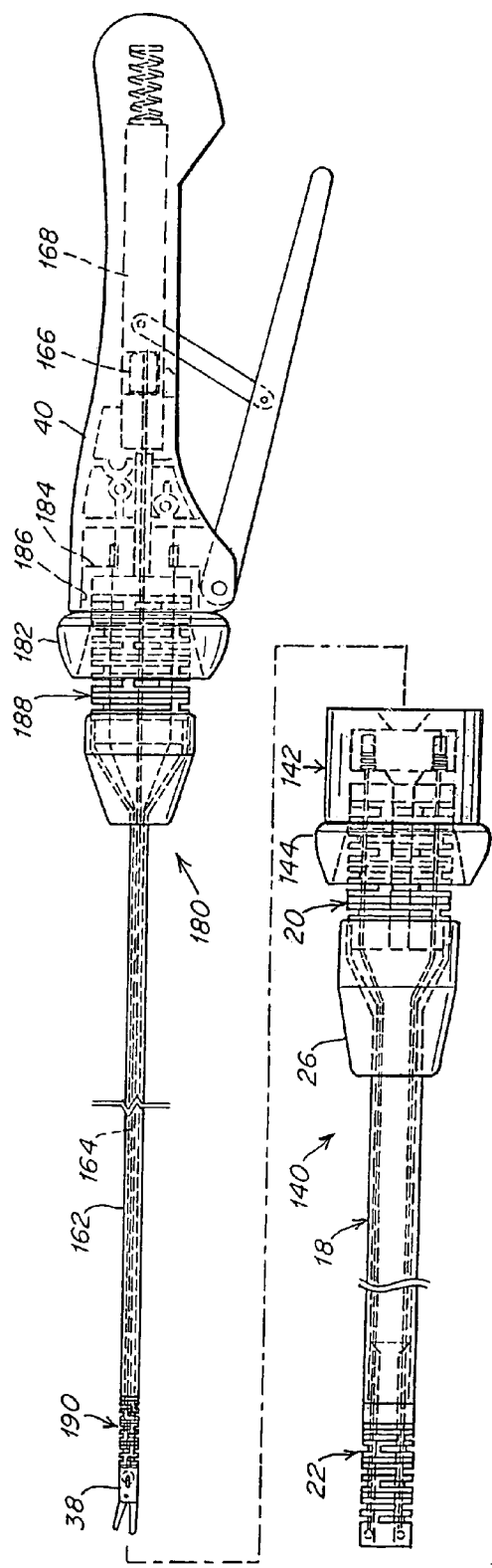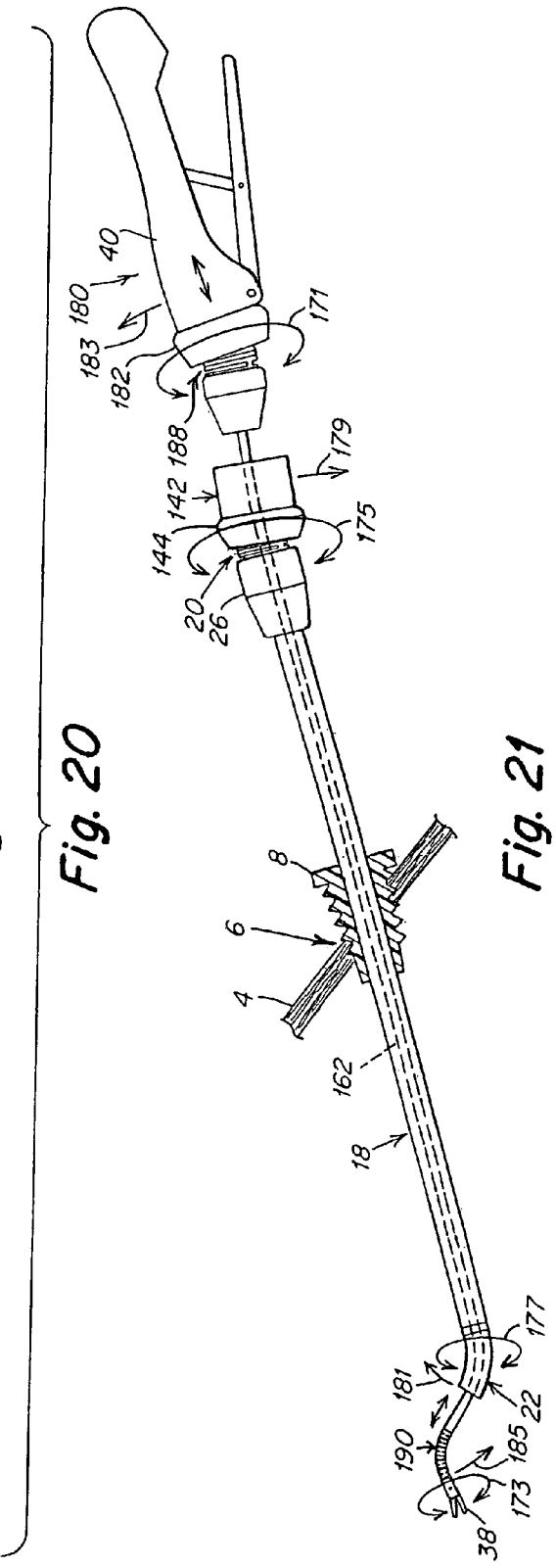

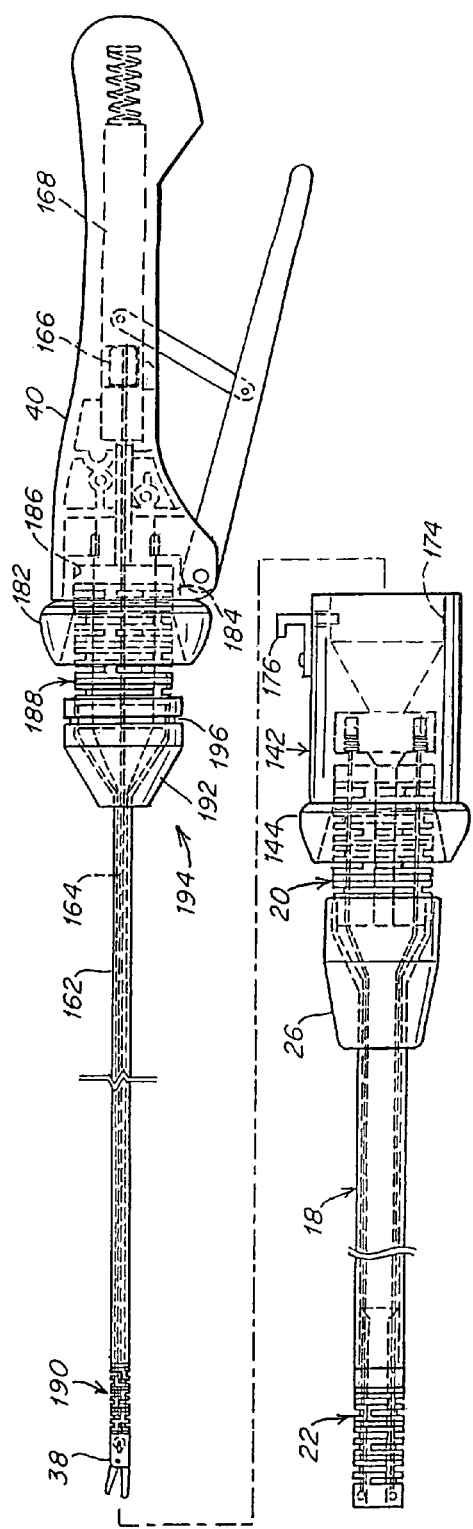
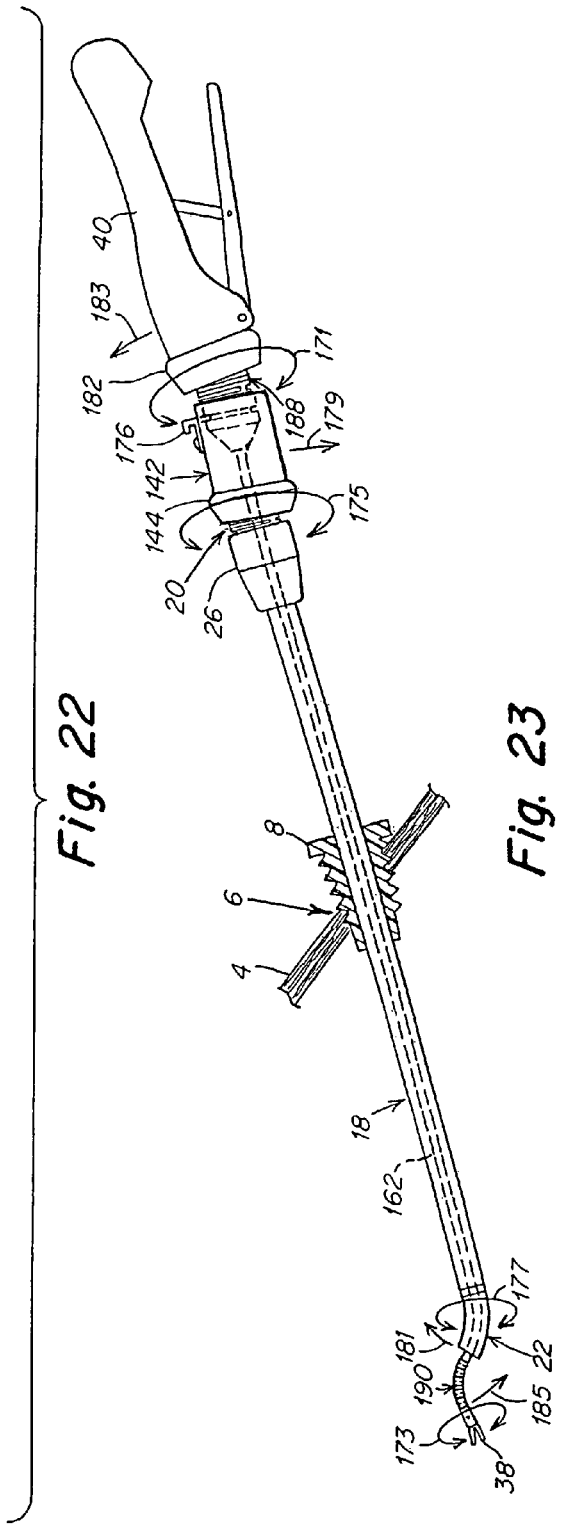
Fig. 22
Fig. 23

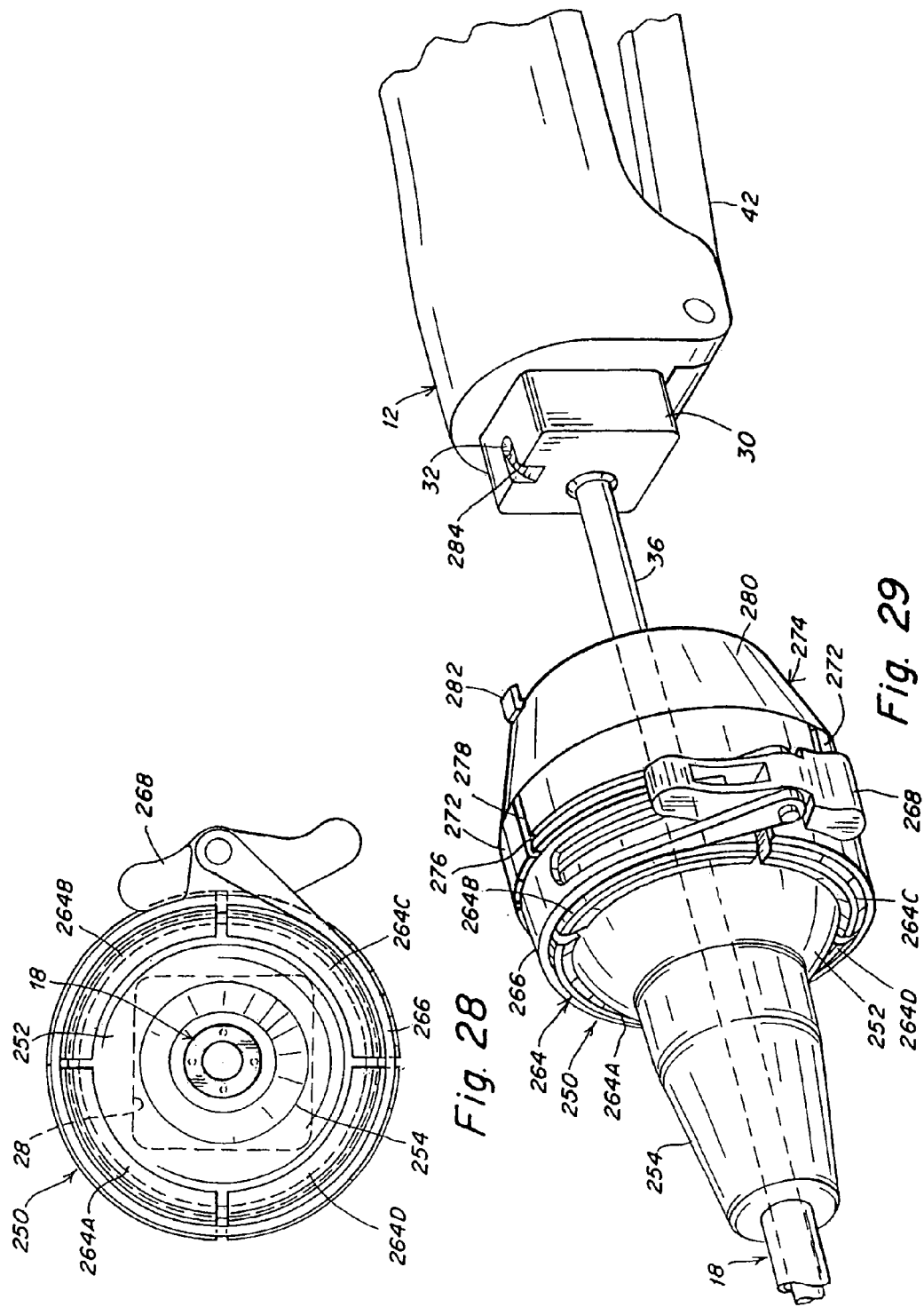

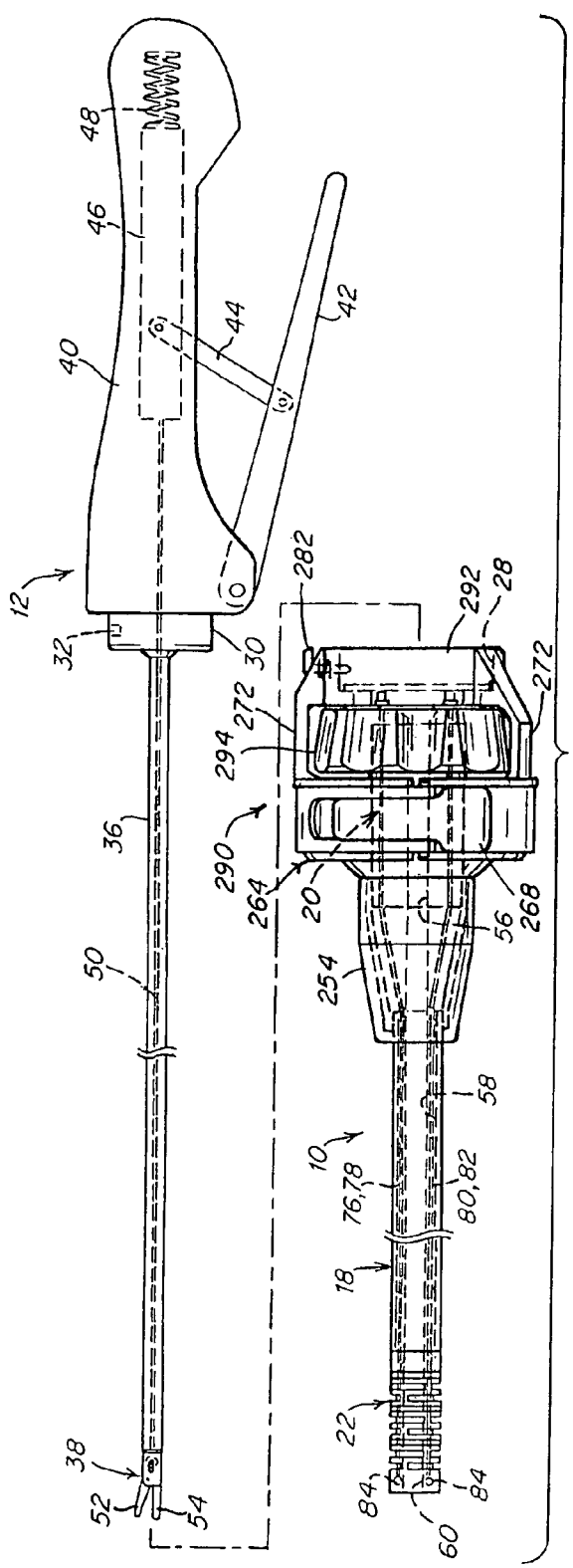
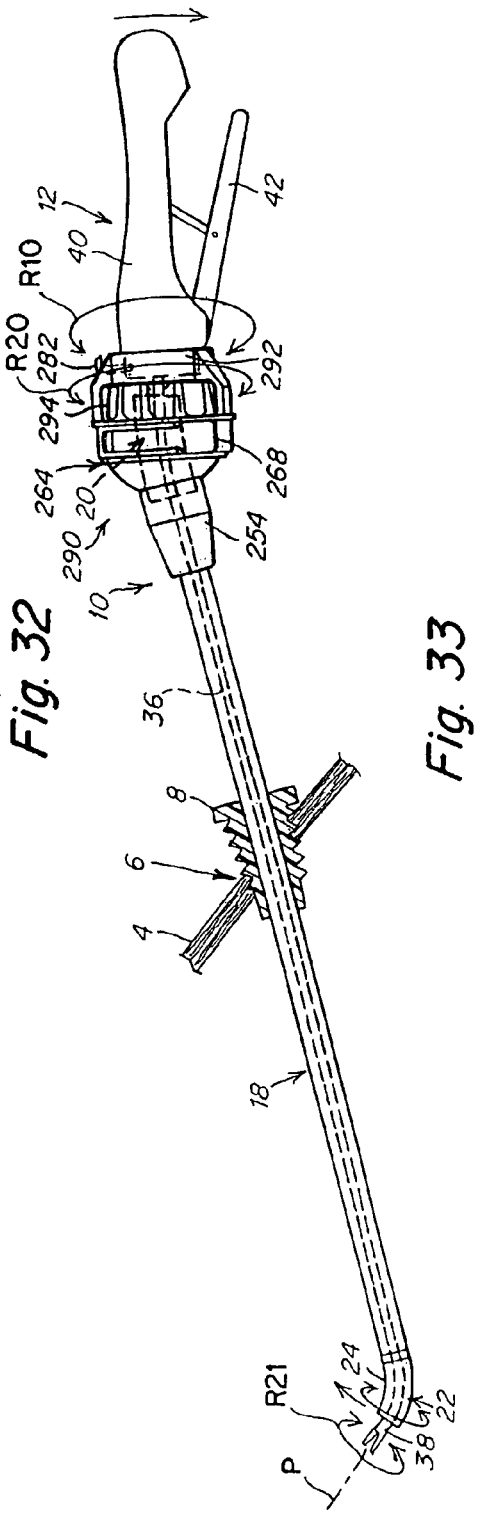
Fig. 32
Fig. 33

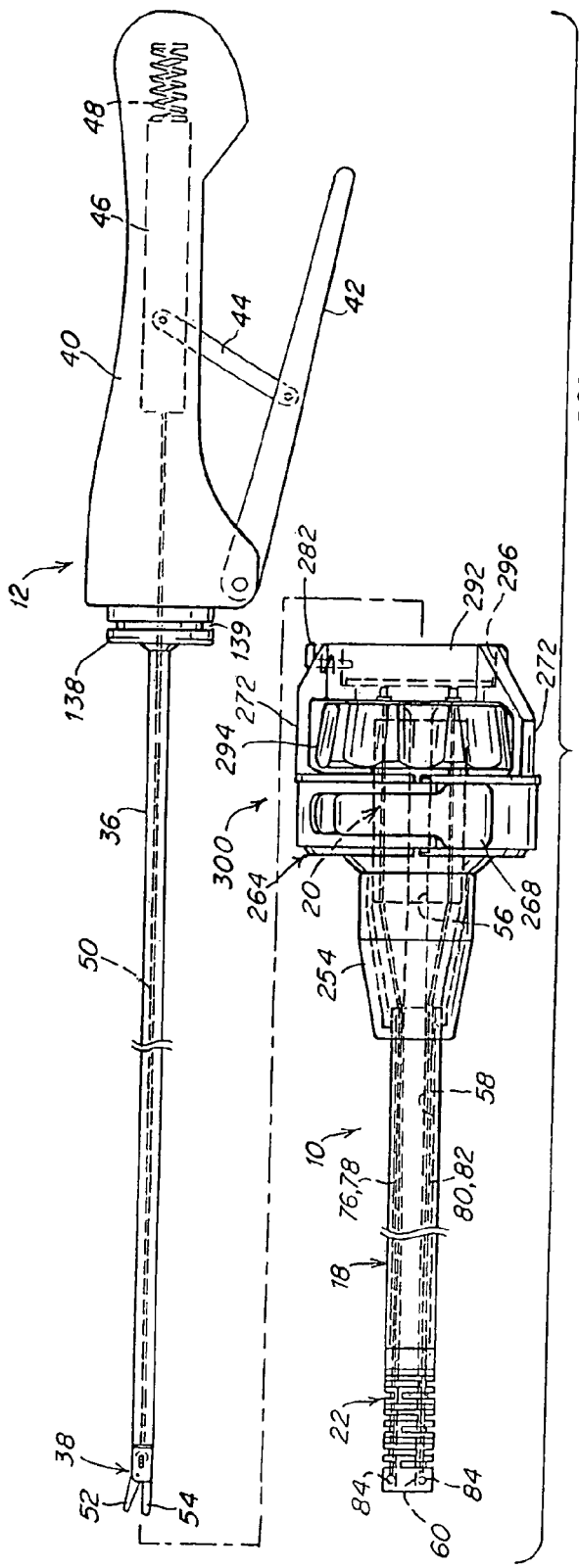
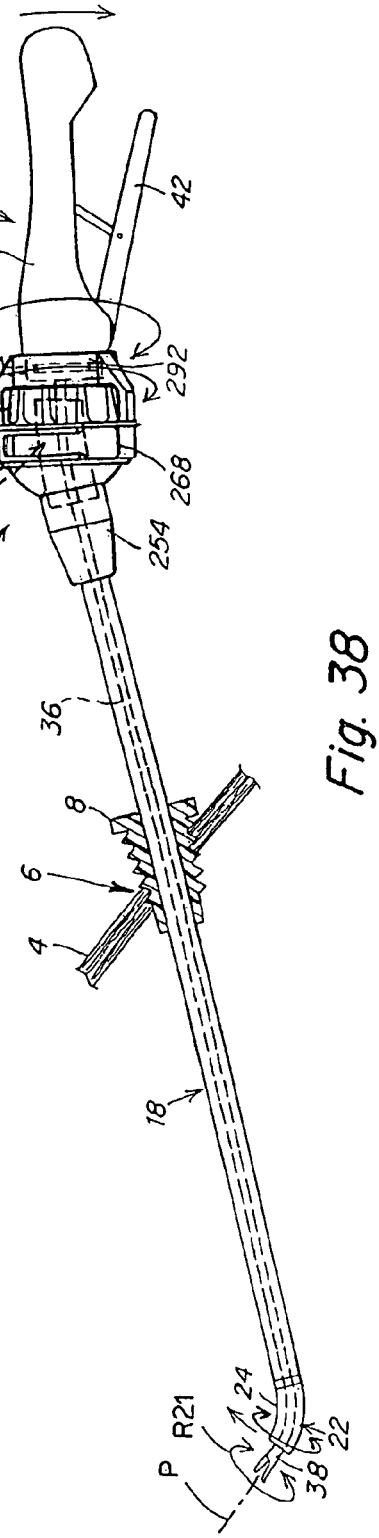
Fig. 37
Fig. 38

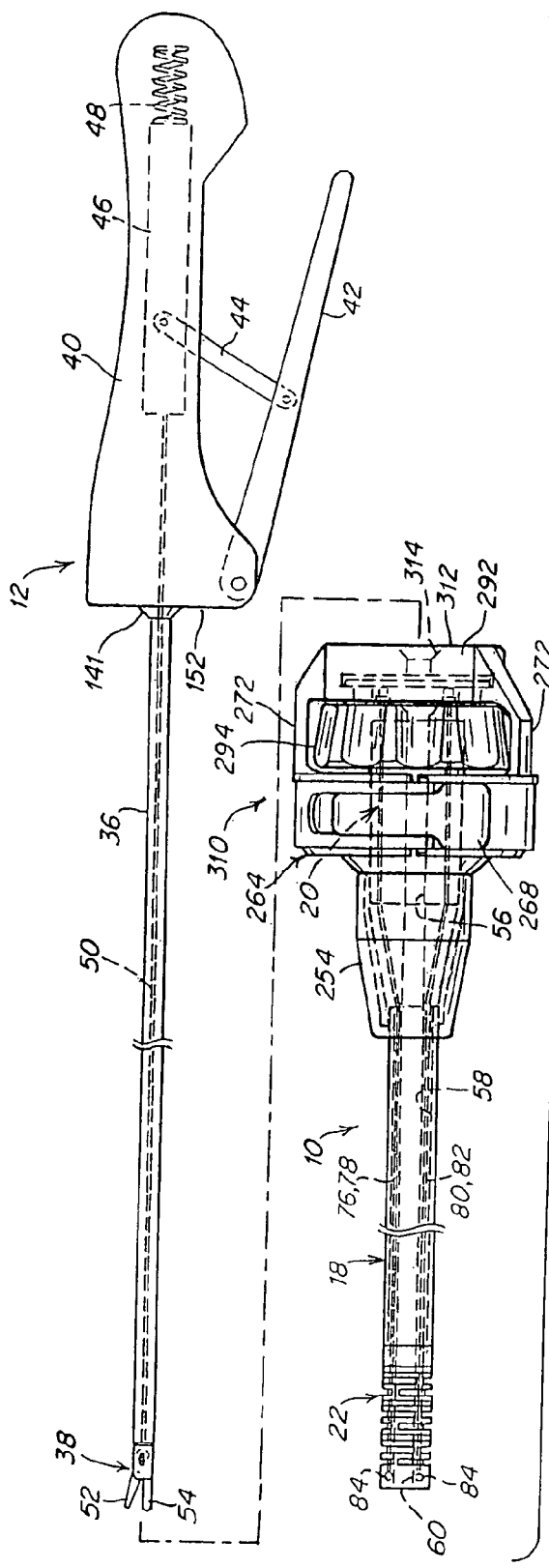
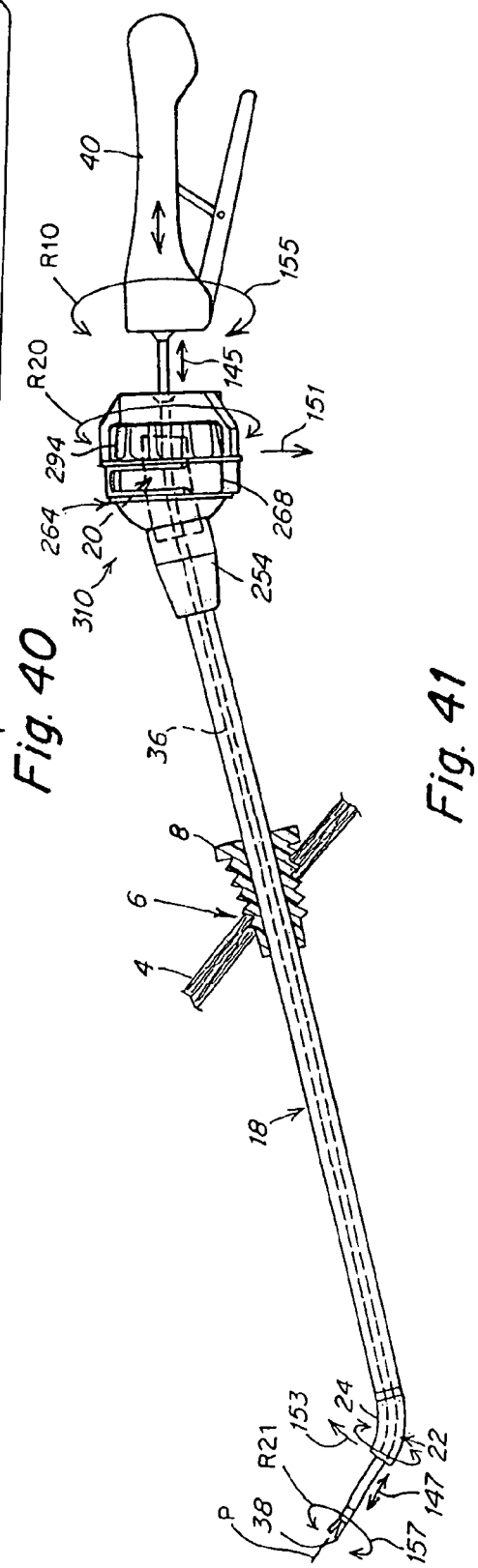
Fig. 40
Fig. 41

SURGICAL INSTRUMENT GUIDE DEVICE

RELATED APPLICATIONS

The present application is a continuation-in-part of U.S. application Ser. No. 11/242,642 filed Oct. 3, 2005 now U.S. Pat. No. 7,842,028, which, in turn, claims priority to earlier filed U.S. Provisional Application 60/700,776, filed on Jul. 20, 2005. The present invention also relates to earlier filed U.S. application Ser. No. 10/822,081, filed on Apr. 12, 2004 which, in turn, claims priority to U.S. Provisional Application Ser. No. 60/515,560, filed on Oct. 30, 2003, as well as U.S. application Ser. No. 11/185,911, filed on Jul. 20, 2005 which, in turn, claims priority to U.S. Provisional Application Ser. No. 60/671,189, filed on Apr. 14, 2005. The content of all of the aforementioned applications are hereby incorporated by reference herein in their entirety.

TECHNICAL FIELD

The present invention relates in general to surgical instruments, and more particularly to manually-operated surgical instruments that are intended for use in minimally invasive surgery or other forms of surgical procedures or techniques. Even more particularly the present invention relates to a guide apparatus for a medical instrument. The instrument described herein may be used for laparoscopic procedures, however, it is to be understood that the instrument and guide of the present invention can be used for a wide variety of other procedures, including intraluminal procedures.

BACKGROUND OF THE INVENTION

Endoscopic and laparoscopic instruments currently available in the market are extremely difficult to learn to operate and use, mainly due to a lack of dexterity in their use. For instance, when using a typical laparoscopic instrument during surgery, the orientation of the tool of the instrument is solely dictated by the locations of the target and the incision. These instruments generally function with a fulcrum effect using the patient's own incision area as the fulcrum. As a result, common tasks such as suturing, knotting and fine dissection have become challenging to master. Various laparoscopic instruments have been developed over the years to overcome this deficiency, usually by providing an extra articulation often controlled by a separately disposed control member for added control. However, even so these instruments still do not provide enough dexterity to allow the surgeon to perform common tasks such as suturing, particularly at any arbitrarily selected orientation.

The above identified related earlier filed applications describe an improved instrument employing bendable section on the instrument itself.

An object of the present invention is to provide a guide device or apparatus that can be used with either conventional or the above identified instruments for laparoscopic, endoscopic or other surgical procedures and that allows the surgeon to readily manipulate the tool or working end of the surgical instrument with greater dexterity.

Another object of the present invention is to provide an improved surgical instrument and guide that has a wide variety of applications, including, but not limited to, through incisions, through natural body orifices or extending intraluminally.

Still another object of the present invention is to provide and improved surgical instrument and associated guide wherein the guide has a locking feature to keep the instrument in a selected position.

SUMMARY OF THE INVENTION

To accomplish the foregoing and other objects, features and advantages of this invention, there is provided an instrument guide device that is comprised of an elongated guide shaft having proximal and distal ends and including an instrument lumen for receiving therethrough a manually operated instrument having an instrument shaft and handle. A distal bendable member is disposed at the distal end of the guide shaft and a proximal bendable member id disposed at the proximal end of the guide shaft. Actuation means extends between the distal and proximal bendable members for providing a bending of the distal bendable member controlled from the proximal bendable member. The proximal bendable member is controlled from the manually operated instrument to cause a corresponding bending of the distal bendable member.

In accordance with other aspects of the present invention there is provided an instrument guide device wherein the actuation means is constructed and arranged so that a bending of the proximal bendable member causes a like direction bending of the distal bendable member, or, alternatively, the actuation means is constructed and arranged so that a bending of the proximal bendable member causes an opposite direction bending of the distal bendable member. The proximal bendable member is preferably moveable in any direction. A grip may be disposed between the proximal bendable member and the handle of the instrument and constructed and arranged to have a passage through which the instrument shaft extends. The grip may be formed as two pieces including a grip portion and a rotation knob and the grip and knob portions are supported for relative rotation therebetween. Means may be provided for securing the instrument handle to the grip. The bendable members may each comprise a unitary slotted structure having a plurality of discs separated by slots. The guide shaft may be rigid, flexible or partially flexible. The instrument guide device may include a plurality of proximal bendable members and a plurality of distal bendable members. The actuation means may comprise a plurality of cables that interconnect proximal and distal bendable members. The guide shaft may have at least two lumens for respectively accommodating separate instrument shafts. The instrument that is inserted in the guide device may have instrument proximal and distal bendable members.

In an other embodiment of the present invention there is provided a surgical instrument assembly that comprises an elongated instrument shaft having proximal and distal ends, a working member coupled from the distal end of the instrument shaft, a control handle disposed at the proximal end of the instrument shaft and a guide member for receiving the instrument shaft. The guide member includes a guide shaft, a distal motion means at the distal end of the guide shaft, a proximal motion means at the proximal end of the guide shaft and actuation means extending between the distal and proximal motion means. The working member extends beyond a distal end of the guide shaft at an operative site. Any deflection of the proximal motion means causes a corresponding deflection of the distal motion means for control of the working member.

In accordance with still other aspects of the present invention there is provided a surgical instrument assembly in which the distal motion means comprises a distal bendable member and the proximal motion means comprises a proximal bendable member that is moveable in any direction. A grip may be disposed between the proximal bendable member and the handle of the instrument and constructed and arranged to have a passage through which the instrument shaft extends. The grip may be formed as two pieces including a grip portion and a rotation knob and the grip and knob portions are supported for relative rotation therebetween. The proximal bendable member may comprise a unitary slotted structure having a plurality of discs separated by slots and further including a plurality of ribs interconnecting adjacent discs, the ribs being disposed at intervals about the member of less than 90 degrees.

In a further embodiment of the present invention there is provided a surgical instrument that is comprised of an elongated instrument shaft having proximal and distal ends, a working member disposed at the distal end of the instrument shaft and a control handle disposed at the proximal end of the instrument shaft. The working member is coupled to the distal end of the elongated instrument shaft via a distal motion member. The control handle is coupled to the proximal end of the elongated instrument shaft via a proximal bendable member. Actuation means extends between the distal and proximal members whereby any deflection of the control handle with respect to the elongated instrument shaft causes a corresponding bending of the distal motion member for control of the working member. At least the proximal bendable member comprises a unitary slotted structure having a plurality of discs separated by slots.

In accordance with still other aspects of the present invention there is provided an instrument guide device in which the distal motion member also comprises a bendable member formed as a unitary slotted structure having a plurality of discs separated by slots. The proximal bendable member may include a plurality of ribs interconnecting adjacent discs, the ribs being disposed at intervals about the member of less than 90 degrees. The ribs may be disposed at an interval on the order of 60 degrees.

In accordance with a locking feature there is provided a guide device for controlling a manually operated medical instrument that includes at least a handle, instrument shaft and distal tool. The guide device comprises; an elongated guide shaft having proximal and distal ends and including an instrument lumen for receiving therethrough the manually operated medical instrument; a distal bendable member disposed at the distal end of the elongated guide shaft; a proximal bendable member disposed at the proximal end of the elongated guide shaft; and actuation means extending between the distal and proximal bendable members and providing a bending of the distal bendable member controlled from the proximal bendable member. The proximal bendable member is controlled from the manually operated medical instrument to cause a corresponding bending of the distal bendable member and control of the distal tool. A locking mechanism fixes the position of the distal tool at a selected position and having locked and unlocked states. The locking mechanism includes a ball and socket arrangement disposed about said proximal motion member and a cinch member for locking the ball and socket arrangement.

In accordance with other aspects of this embodiment the actuation means may be constructed and arranged so that a bending of the proximal bendable member causes a like direction or opposite direction bending of the distal bendable member; the proximal bendable member is moveable in any direction; a grip is disposed between the proximal bendable member and the handle of the manually operated medical instrument and constructed and arranged to have a passage through which the manually operated medical instrument shaft extends; the grip may be formed as one or two two pieces including a grip portion and a rotation knob and the grip and knob portions are supported for relative rotation therebetween; means may be provided for securing the manually operated medical instrument handle to the grip portion; the ball and socket arrangement comprises a grip portion and a ball member having a partially spherical portion that mates with a concave socket in the grip portion; the grip portion has the socket formed therein and the cinch member includes an annular cinch ring that is disposed about the grip portion; a locking lever is provided on the cinch ring having opposed locked and unlocked positions; the grip portion may include a split hub that is compressable by the cinch ring as the cinch ring is locked via the locking lever; the guide device may be rotational relative to the manually operated medical instrument; or the manually operated medical instrument may be slideable linearly relative to the guide device.

In accordance with a further embodiment of the invention there is provided a guide device for controlling a manual instrument that has a handle instrument shaft and distal tool, comprising, a proximal control handle, a guide shaft and proximal and distal bendable members that respectively intercouple the proximal and distal bendable members, cable actuation means disposed between the bendable members, for controlling the positioning of the distal tool, and a locking mechanism having locked and unlocked positions with the locking mechanism including a ball and socket arrangement disposed about the proximal motion member and a cinch member for locking the ball and socket arrangement. The locking mechanism may comprise a ball member and a compressible hub that defines a socket member. The hub is preferably a split hub and the locking mechanism further includes a cinch ring disposed about the split hub and a locking lever mounted on said cinch ring for closing said cinch ring about said hub to lock the hub against said ball member. The cinch ring preferably interlocks with the hub but is able to rotate relative thereto when in the unlocked position. A rotation knob may be supported by the hub.

DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings, in which:

FIG. 1 is an exploded side view of a first embodiment of a surgical instrument and guide device using a rigid guide tube shaft;

FIG. 2 is a view of the proximal end of the guide device of FIG. 1, as taken along line 2-2 of FIG. 1;

FIG. 3 is a schematic side view of the instrument and guide assembly in use as inserted through a patient's skin at an incision;

FIG. 4 is a fragmentary enlarged cross-sectional side view of the assembly of FIG. 3;

FIG. 5 is a cross-sectional view of the proximal bendable member, as taken along line 5-5 of FIG. 4;

FIG. 6 is an exploded perspective view of the guide apparatus or device illustrated in FIGS. 1-5;

FIG. 7 is a schematic cross-sectional side view illustrating the bending action of the assembly of FIG. 4;

FIG. 8 is a schematic cross-sectional side view illustrating an alternate bending action;

FIG. 12 is an exploded side view of a fourth embodiment of the guide device used with a second embodiment of a surgical instrument;

FIG. 13 is a view of the proximal end of the guide device of FIG. 12, as taken along line 13-13 of FIG. 12;

FIG. 14 is a schematic side view of the instrument and guide assembly of FIG. 12 in use;

FIG. 15 is an exploded side view of a fifth embodiment of the guide device with a third embodiment of the surgical instrument;

FIG. 16 is a view of the proximal end of the guide device of FIG. 15, as taken along line 16-16 of FIG. 15;

FIG. 17 is a schematic side view of the instrument and guide assembly of FIG. 15 in use as inserted through a patient's skin at an incision;

FIG. 18 is an exploded side view of a sixth embodiment of the guide device and a fourth embodiment of the surgical instrument;

FIG. 19 is a schematic side view of the instrument and guide assembly of FIG. 18 in use as inserted through a patient's skin at an incision;

FIG. 20 is an exploded side view of the fifth embodiment of the guide device as used with a fifth embodiment of the surgical instrument;

FIG. 21 is a schematic side view of the instrument and guide assembly of FIG. 20 in use as inserted through a patient's skin at an incision;

FIG. 22 is an exploded side view of the sixth embodiment of the guide device as used with a sixth embodiment of the surgical instrument;

FIG. 23 is a schematic side view of the instrument and guide assembly of FIG. 22 in use as inserted through a patient's skin at an incision;

FIG. 28 is an end view as seen along line 28-28 of FIG. 26;

FIG. 29 is a partially exploded perspective view of the manually operated instrument being inserted into the guide member;

FIG. 32 is an exploded side view of still another embodiment of the manual instrument and guide member and including a locking feature;

FIG. 33 is a schematic side view of the instrument of FIG. 32 and in use;

FIG. 37 is an exploded side view of still another embodiment of the manual instrument and guide member and including a locking feature;

FIG. 38 is a schematic side view of the instrument of FIG. 37 and in use;

FIG. 40 is an exploded side view of a further embodiment of the manual instrument and guide member and including a locking feature;

FIG. 41 is a schematic side view of the instrument of FIG. 40 and in use; and

DETAILED DESCRIPTION

Figure 9:
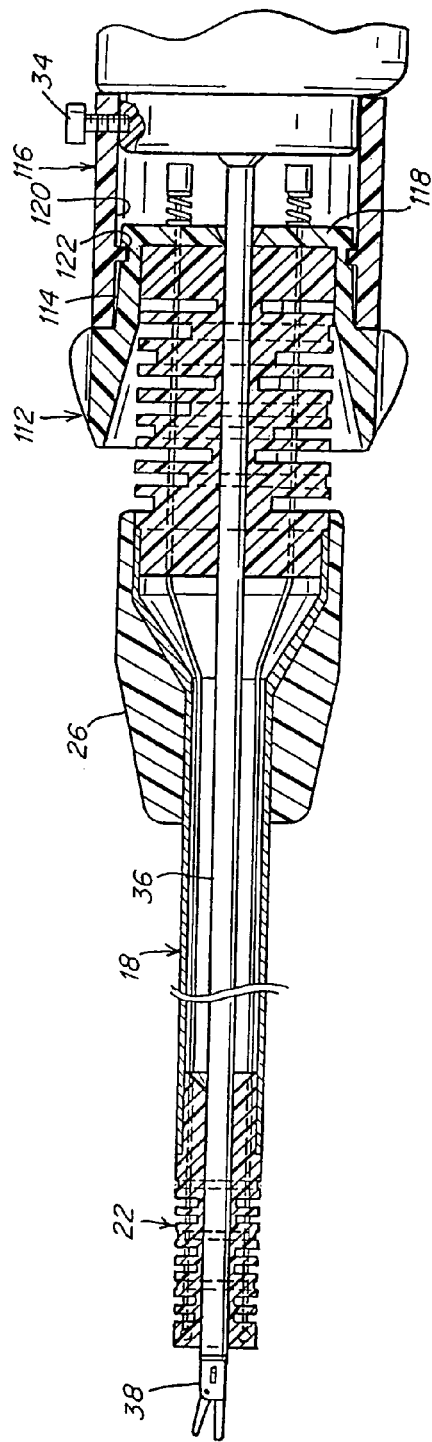
FIG. 9 is a fragmentary cross-sectional side view similar to that shown in FIG. 4, but illustrating a second embodiment of the guide assembly having an added rotational feature.

The instrument and guide member of the present invention may be used to perform minimally invasive procedures or virtually any other types of surgical or medical procedures. "Minimally invasive procedure" refers herein to a surgical procedure in which a surgeon operates through a small cut or incision, the small incision being used to access the operative site. In one embodiment, the incision length ranges from 1 mm to 20 mm in diameter, preferably from 5 mm to 10 mm in diameter. This procedure contrasts those procedures requiring a large cut to access the operative site. Thus, the instrument assembly is preferably used for insertion through such small incisions and/or through a natural body lumen or cavity, so as to locate the instrument at an internal target site for a particular surgical or medical procedure. The introduction of the surgical instrument assembly into the anatomy may also be by percutaneous or surgical access to a lumen or vessel, or by introduction through a natural orifice in the anatomy. Also, even though the instrument assembly is preferably used for MIS surgery it can also be used for open surgery or any other surgical or medical procedures.

In addition to use in a laparoscopic procedure, the instrument and guide of the present invention may be used in a variety of other medical or surgical procedures including, but not limited to, colonoscopic, upper GI, arthroscopic, sinus, thoracic, transvaginal and cardiac procedures. Depending upon the particular procedure, the instrument shaft may be rigid, semi-rigid or flexible.

Although reference is made herein to a surgical instrument and guide, it is contemplated that the principles of this invention also apply to other medical instruments, not necessarily for surgery, and including, but not limited to, such other implements as catheters, endoscopes, optics, as well as diagnostic and therapeutic instruments and implements.

Still another aspect of the surgical guide instrument of the present invention is the ability to adapt the instrument and guide to a wide variety of medical procedure. This includes, but is not limited to, access to a body cavity such as through an incision or intraluminal use such as through a natural body aperture to a body lumen. The introduction of the instrument into the anatomy may also be by percutaneous or surgical access to a lumen, cavity or vessel, or by introduction through a natural orifice in the anatomy.

The concepts of the present invention relate to the use of a manually controllable guide member or device through which either a conventional instrument shaft may be inserted or through which a novel instrument may be inserted, such as the novel instrument described in my previously identified related pending applications. With the use of the guide member of the present invention, the user can insert the instrument shaft through the guide member and then use the bendable members of the guide member to control the manipulation of the instrument. Thus, by deflecting the instrument, once positioned in the guide member, this causes a deflection or bending at the proximal bendable member that is transferred to the distal bendable member (usually by cabling) to control the positioning of the distal tool. This bending control at the guide member is preferably in all directions.

It should be noted that the amount of guide member bending motion produced at the distal bending member is determined by the dimension of the proximal bendable member in comparison to that of the distal bendable member. In the disclosed embodiment the proximal bendable member may be approximately three times the diameter of the distal bendable member, and as a result, the motion produced at the distal bendable member is about three times the magnitude of the motion at the proximal bendable member. Although FIG. 3 shows only the side view where only pitch motion is illustrated, it should be noted that the proximal bendable member can be bent in any and all directions controlling the distal bendable member to bend in either the same or an opposite direction, but in the same plane. As a result, as depicted in FIG. 3 the surgeon is able to roll the instrument tool about its longitudinal axis at any orientation simply by a rolling action at the proximal bendable member, controlled primarily by manipulation of the handle of the inserted instrument bearing against the guide member.

In this description reference is made to bendable members. These members may also be referred to as turnable members or flexible members. In the descriptions set out herein, terms such as bendable section, bendable segment, bendable motion member, or turnable member refer to an element of the guide instrument that is controllably bendable in comparison to an element that is pivoted at a joint. The bendable elements of the present invention enable bending in any direction without any singularity and that is further characterized by a ready capability to bend in any direction, all with a single unitary or uni-body structure. A definition of these bendable motion members is—a guide element, formed either as a controlling means or a controlled means, and that is capable of being constrained by tension or compression forces to deviate from a straight line to a curved configuration without any sharp breaks or angularity.

The first embodiment is described in FIGS. 1-6. The guide member or instrument 10 has a proximal bendable member 20 and distal bendable member 22 and receives the instrument 12 such as depicted in FIG. 3 in the inserted position of the instrument 12, depicted as the assembled instrument system 14. The instrument 12 may be conventional and is secured in the guide member 10 so that motions at the instrument handle 40 are essentially transferred through the guide member 10 to control the positioning of the end effector. In other words a deflection of the handle 40 causes a bending of the proximal bendable member 20 (as in FIG. 3) which, in turn, bends the distal bendable member 22 to control the placement of the tool or end effector. This first embodiment also includes a grip 16 that provides the interface between the handle 40 and the proximal bendable member 20. The grip 16, in this particular embodiment, is one-piece so the only rotation of the instrument is by rotating the entire instrument and guide member. The instrument 12 is locked to the guide member 10 so there is no linear motion of the instrument relative to the guide member.

Referring to FIG. 1, the surgical instrument 12 may be considered as of conventional design and is comprised of a handle 40 at the proximal end of the instrument, an elongated flexible instrument shaft 36 and a tool or end effector 38 disposed at the distal end of the surgical instrument 12. In the disclosed embodiment the instrument shaft 36 is preferably constructed so as to be at least partially flexible or bendable so as to sufficiently bend with the bending of the bendable members of the guide member 10. The tool 38 is illustrated as including a fixed jaw 54 and a moveable jaw 52. The tool 38 is actuated by means of an actuation cable 50 that extends through the instrument shaft 36 and is controlled from the slider 46 and return spring 48. A lever 42 operates the slider 46 through the linkage or transfer bar 44. The closure of the lever 42 pulls the cable 50 to close the jaws 52, 54.

In the drawings a set of jaws is depicted, however, other tools or devices may be readily adapted for use with the instrument of the present invention. These include, but are not limited to, cameras, detectors, optics, scope, fluid delivery devices, syringes, etc. The tool may include a variety of articulated tools such as jaws, scissors, graspers, needle holders, micro dissectors, staple appliers, tackers, suction irrigation tools and clip appliers. In addition, the tool may include a non-articulated tool such as a cutting blade, probe, irrigator, catheter or suction orifice.

In FIGS. 1-6, the guide member or guide instrument 10 is depicted separately from the surgical instrument 12 as in FIG. 1. In FIG. 3, there is shown the assembled system 14 with the instrument having been inserted into and through the guide member 10. In FIG. 3 note that the guide member shaft 18 extends through the cannula 8 at the insertion site 6 of the patient's skin 4. The end effector or tool 38 is disclosed in FIG. 3 as extending from the distal bendable member 22. FIG. 3 also shows a protective sheath 24 that may extend about the distal flex member 22.

The guide member 10, in addition to including the guide shaft 18, also includes the proximal flexible or bendable member 20 and the distal flexable or bendable member 22. An adaptor cover 26 is disposed about a portion of the proximal bendable member 20. The adaptor cover 26 includes a funnel or conical-shaped portion 96 (see FIG. 6) for receiving ends of the proximal bendable member 20 and the guide shaft 18. The grip 16 of the guide member 10 receives the other end of the proximal bendable member 20. The grip 16 is preferably a single piece structure having a cavity 28 for receiving the boss 30 of the conventional instrument 12. The boss 30 may also be provided with a recess 32 for receiving a locking screw 34 that extends through the grip 16 into the cavity 28 and into the recess 32. The use of the locking screw 34 secures the instrument 12 within the guide member 10. Motions of the instrument are thus directly transferred to the grip 16 and, in turn, to the proximal bendable member 20. The length of the guide member is selected so that the instrument tool extends beyond the end of the guide member, as depicted in FIG. 3.

This first embodiment also discloses the details of the proximal and distal bendable members 20 and 22, particularly in FIGS. 4-6. Bendable member 20 has a central passage 56 through which the instrument shaft 36 can extend. FIG. 4 also illustrates the lumen 58 defined by the guide shaft 18 with the instrument shaft 36 extending therethrough. Similarly, the distal bendable member 22 includes a passage 60 for receiving the instrument shaft 36. In FIG. 4 the guide shaft 18 is shown as rigid, but could also be partially rigid or flexible. The guide shaft 18 may be made of a light weight metal material or of plastic.

The grip 16 includes a cavity 62 (see FIG. 6) for receiving one end of the proximal bendable member 20. This bendable member 20 is seated at the end wall 64 of the grip 16. The wall 64 has a tapered or conical passage 66 for receiving the instrument shaft 36. As depicted in FIG. 6, there are also provided several passages 68 for cabling. The grip 16 also includes a cavity 70 for the anchors 86 and springs 88. This includes a plurality of proximal anchors 86 and related springs 88. The springs 88 are for tensioning the associated cables 76-82. The distal bendable member 22 includes an extending end 94 for receiving the distal anchors 84 that secure the distal ends of the actuation cables 76-82. The grip 16 also preferably includes a raised lip 72 that is useful in grasping the guide grip 16. The raised lip 72 preferably has spaced finger grooves 74.

The control between the proximal and distal bendable members is carried out primarily by means of a set of cables that extend between these bendable members. A bending at the proximal bendable member causes a pulling of one or more cables while there is a relaxing of other opposed cables causing a corresponding bending action at the distal bendable member. The cabling that is used includes flexible cables 76, 78, 80 and 82 that extend between the proximal and distal bendable members. A plurality of distal anchors 84 are used at the distal end of the cabling. Cable passages 90 are provided in the proximal bendable member 20, and cable passages 92 are provided in the distal bendable member 22. The passages 90 and 92 accommodate these cables. Also, guide discs (not shown) may be provided along the cables, particularly within the guide shaft 18 so assure that the cables are maintained in position as they extend from one end of the guide shaft to the other end.

The proximal bendable member 20 is comprised of a series of adjacent discs 98 that define therebetween spaces or slots 100. Connecting ribs 102 extend between adjacent discs 98. FIG. 5 depicts the location of the ribs 102. In a similar manner, the distal bendable member 22 includes a series of discs 104 that define therebetween slots or spaces 106. Ribs 108 extend between adjacent discs 104. For further details of the bendable members and the prefered relationship between the disks, slots and ribs, refer to application Ser. No. 11/185,911, filed on Jul. 20, 2005, the content of which is hereby incorporated by reference herein.

FIGS. 7 and 8 depict the guide member with the instrument inserted therein and also depicts the various motions that occur depending upon the position of the control cables that control the bending actions. In FIG. 7, a downward movement of the proximal bendable member 20 causes an upward movement of the distal bendable member 22. Alternatively, in FIG. 8 a downward movement of the proximal bendable member 20 causes a downward movement of the distal bendable member 22. This all occurs by virtue of the cabling being either extended or retracted as the proximal bendable member is manipulated. The different direction bending comes about by either having the cabling straight, as in FIG. 7 or crossed 180 degrees, as in FIG. 8. In FIGS. 7 and 8, the instrument handle is shown fixed to the grip portion 16, and by manipulating of the handle, this causes a direct manipulation of the grip portion, which, in turn, controls the bending at the proximal bendable member. The bending at the proximal bendable member, in turn, controls the positioning of the distal bendable member and end effector.

Figure 10:
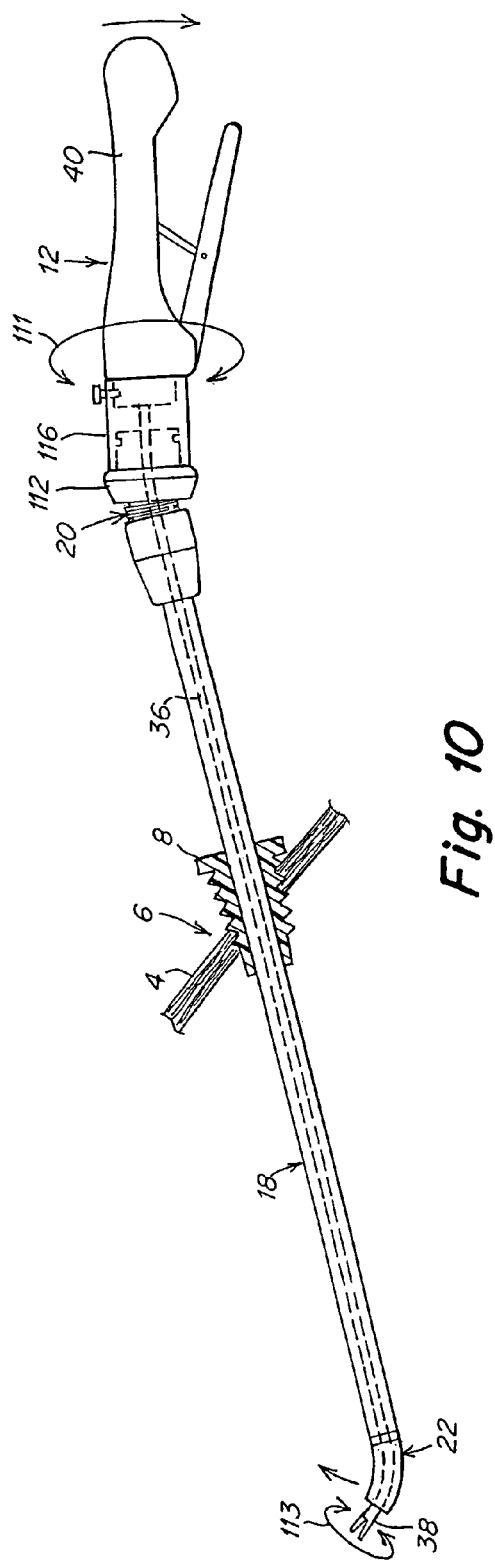
FIG. 10 is a schematic side view of the guide assembly of FIG. 9 in use with the jaw end effector of FIG. 1.

A second embodiment of the present invention is shown in FIGS. 9 and 10. This uses a two-piece grip 116 with a rotation knob 112. This embodiment allows the same bending action as in the first embodiment via proximal and distal bendable members, but additionally allows the user to rotate the guide member relative to the grip portion 116. This rotation action causes rotation of the bendable members 20, 22 and guide shaft 36 on their axes.

The embodiment of FIGS. 9 and 10 also illustrates the instrument handle being fixedly supported to the grip 116. In this particular embodiment, rather than a single-piece grip, there is provided an essentially two-piece grip that also includes the rotation knob 112. A boss 114 is provided on the knob 112 terminating in an end wall 118 of the rotation knob 112. The grip 116 is provided with a cavity 120 for receiving the boss 114. Retention means 122 (annular innwardly extending rib) extends from the grip 116 into an annular slot. In this way the rotation knob 112 is engaged with the grip 116 but is freely rotatable relative to the grip 116. FIG. 10 also shows the arrow 111 indicating rotation of the instrument handle 12 relative to the knob 112. Arrow 113 indicates the corresponding rotation at the end effector 38. Even though the item 112 is refered to as a rotation knob, it is understood that the knob 112 can be held non-rotatable while the grip 116 is rotated relative thereto, such as depicted by the arrows 111, 113 in FIG. 10.

In the first two embodiments of the invention described in FIGS. 1-10, the guide shaft itself may be rigid, flexible or semi-rigid, but is basically depicted as rigid. The instrument shaft itself is preferably at least partially flexible so that it can flex as the proximal end distal members are operated.

Figure 11:
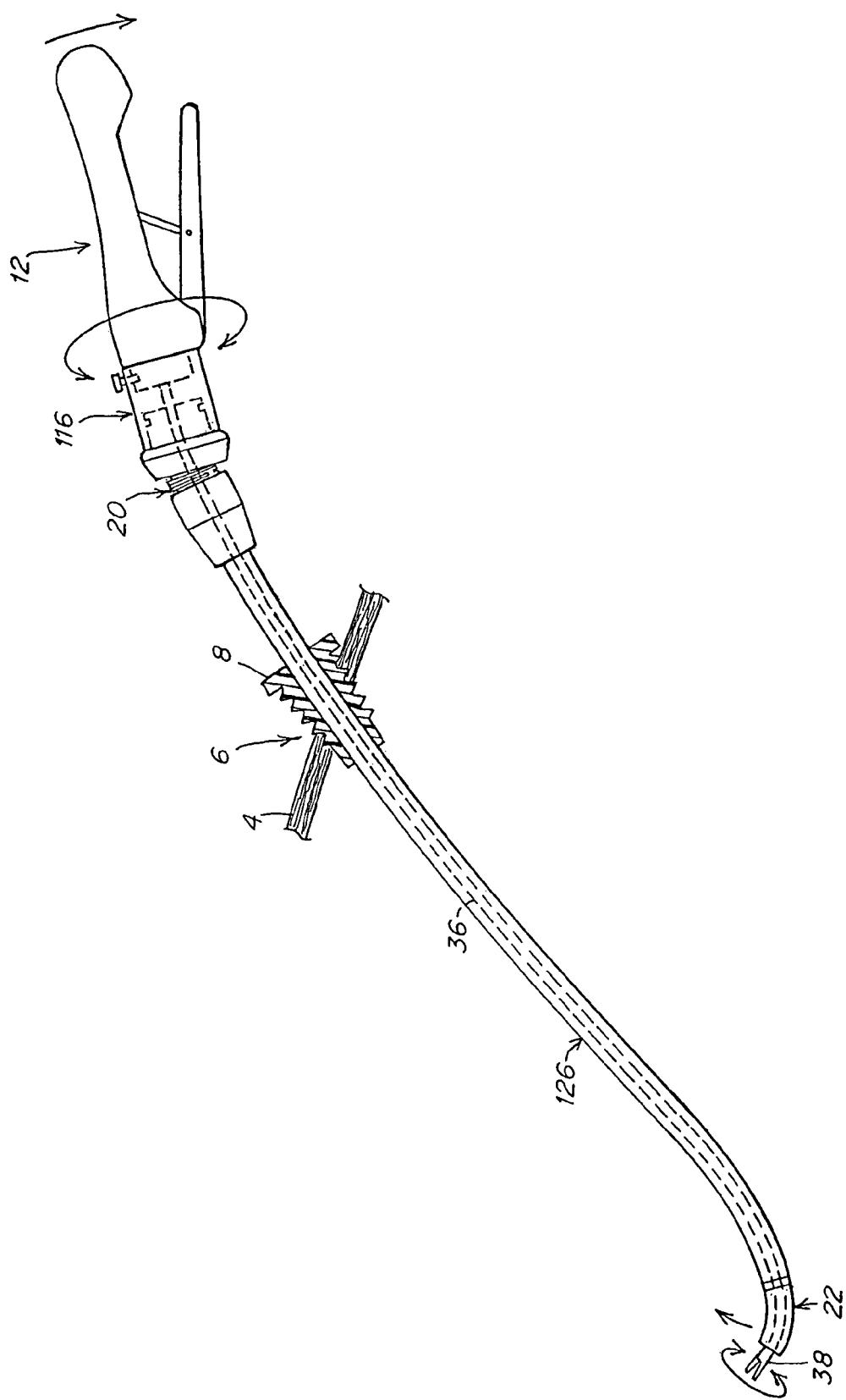
FIG. 11 is a schematic side view of a third embodiment of the guide assembly or device employing a flexible main shaft on the guide device.

A third embodiment of the present invention is shown in FIG. 11 illustrating a flexible or partially flexible guide shaft or tube 126. In the first two embodiments the guide shafts can be rigid or partially flexible and the instrument shaft should be at least partially flexible so as to flex when the bendable members are in action. The embodiment illustrated in FIG. 11 is meant to use a flexible or semi-flexible guide tube 126. This is illustrated as being placed through a cannula 8 at an insertion site 6 of the patient's skin 4, such as for laparoscopic use. FIG. 11 also schematically illustrates the instrument handle 12, the grip and the proximal and distal bendable members 20 and 22. Other than the guide shaft 126, the rest of the guide member may be substantially identical to that described in either FIG. 1-8 or 9 and 10. This particular embodiment also lends itself to use of the instrument and guide assembly intraluminally, such a through an incision or natural body orifice. The end effector may be located in the lumen or the instrument may be positioned so that the end effector is either located in a body cavity or extends through a body lumen or vessel to a cavity.

This third embodiment may also accommodate a conventional endoscope within the guide member. The endoscope is inserted in the guide member. Such an endoscope may have channels for instrumentation, for optics or for other purposes such as irrigation. In that case, the guide member of the present invention can be used for steering the endoscope. This may be quite useful, particularly for intraluminal applications, wherein the endoscope is required to navigate tight curvatures in the anatomic lumen.

A fourth embodiment is shown in FIGS. 12-14 using a one-piece grip that allows the guide member to be rotatable relative to the instrument handle. FIG. 12 is an exploded side view of this fourth embodiment of the guide device used with a second embodiment of a surgical instrument, namely one that includes an interlock between the instrument and guide member. FIG. 13 is a view of the proximal end of the guide device of FIG. 12, as taken along line 13-13 of FIG. 12. FIG. 14 is a schematic side view of the instrument and guide assembly of FIG. 12 in use through an incision. The embodiment of FIGS. 12-14 may be considered as a quick disconnect via the use of a catch that readily enables the instrument to be connected and disconnected with the guide member.

As shown in FIG. 14 rotation can occur of either the handle or grip. The embodiment depicted in FIGS. 12-14 uses a one-piece grip 130 having at one end a raised lip 132 with a catch 133 that extends into the cavity 134. The grip 130 may be substantially the same as the grip depicted in FIGS. 1-6. The boss 138 on the handle 40 has an annular groove 139. The catch 133 is engaged within the annular groove 139 once the instrument is inserted into the guide member 128. In the embodiment of FIGS. 12-14, the guide member 128 is connected with the instrument in a manner where the guide member 128 can be rotated relative to the instrument or vice versa. This occurs by virtue of the catch 133 being readily rotatable within the groove 139 of the instrument handle. In essence, either the grip 130 can be rotated to rotate the entire guide member or the handle of the instrument itself can be rotated. These two different rotations are illustrated by separate arrows 121, 123 in FIG. 14 and corresponding arrows 125, 127 at the distal end of the instrument. The rotation arrow 121 associated with the handle controls the rotation depicted by the distal arrow 127. The rotation arrow 123 associated with the grip controls the rotation depicted by the distal arrow 125.

In FIG. 14 note that the guide member shaft 18 extends through the cannula 8 at the insertion site 6 of the patient's skin 4. The end effector or tool 38 is disclosed in FIG. 14 as extending from the distal bendable member 22. A protective sheath may extend about the distal flex member 22.

A locking device or mechanism may also be associated with the instrument assembly of FIG. 14 in which case the cabling between the proximal and distal bendable members 20, 22 is pinched off holding the bendable members in a fixed bendable orientation. Refer to co-pending application Ser. No. 10/822,081, filed Apr. 12, 2004, which is hereby incorporated by reference in its entirety, for an illustration of a locking mechanism, particularly set forth in FIG. 27. This is described as locking the cables in a particular position so that the orientation of the bendable members are fixed. With this arrangement if the guide member is rotated with the members 20, 22 bent then there is a rotation of the curved distal bendable member, thus displacing the end effector and providing an additional degree of control thereof. This additional degree of control can be provided with several of the embodiments described in this application. Rotation of the instrument itself rotates the end effector within the guide member.

A fifth embodiment is shown in FIGS. 15-17 in which the guide member operates as before, but the additional feature is the support of the instrument that allows a sliding action of the instrument within the guide member, as well as a rotation of the instrument. When the instrument is engaged with the guide member the bending motions can be transferred as in earlier embodiments. In addition the user can move the instrument linearly in and out within the guide member, and can rotate the instrument within the guide member. This embodiment is, in particular, advantageous for intraluminal use of the instrument assembly where is may be desirable to have the capability to linearly move the instrument within a body lumen.

FIG. 15 is an exploded side view of the fifth embodiment of the guide device with a third embodiment of the surgical instrument. FIG. 16 is a view of the proximal end of the guide device of FIG. 15, as taken along line 16-16 of FIG. 15. FIG. 17 is a schematic side view of the instrument and guide assembly of FIG. 15 in use as inserted through a patient's skin at an incision. As mentioned before the instrument assembly may also be used intraluminally in which case the instrument and guide shafts are both flexible along their respective lengths.

In the embodiment of FIGS. 15-17, it is noted that the grip 142 has associated therewith a rotational knob 144. The grip and rotational knob may be supported such as in the manner previously described in FIG. 4. In the illustrated embodiment the grip portion and rotation knob are preferably one-piece. The grip portion 142 includes an end wall 146 and a tapered passage 148 for receiving the instrument shaft 36. The very proximal end 141 of the shaft 36 may be seated in the tapered passage 148. Because the surgical instrument itself is not secured into the grip, it is possible to move the surgical instrument linearly such as in the direction of the arrow 145 in FIG. 17 to provide the corresponding linear translation of the end effector as in the direction of arrow 147 illustrated in FIG. 17. In addition to this linear movement, there is, of course, also bending action as occurs in previous embodiments between the proximal and distal bendable members of the guide tube.

In the embodiment of FIGS. 15-17, the instrument is also capable of being rotated. Arrows in FIG. 17 indicate rotation of the handle and deflection of the proximal bendable member. Corresponding arrows indicate motion at the distal end of the instrument assembly. Arrow 151. indicates a bending at the proximal bendable member 20 and arrow 153 indicates a corresponding bending at the distal bendable member 22. Arrow 155 indicates a rotation at the instrument handle and arrow 157 indicates a corresponding rotation at the end effector. In FIG. 17 the instrument shaft is shown with a certain length, but it is understood that the length thereof may vary depending upon the particular medical use.

FIG. 18 is an exploded side view of a sixth embodiment of the guide device and a fourth embodiment of the surgical instrument. FIG. 19 is a schematic side view of the instrument and guide assembly of FIG. 18 in use as inserted through a patient's skin at an incision. The sixth embodiment shown in FIGS. 18 and 19 uses a one-piece grip including grip portion 142 and knob portion 144. The instrument itself has a rotation knob 156 with a boss 158 that extends within a cavity 160 of the handle 40. FIG. 18 also illustrates the instrument shaft 162. An end effector 38 is also illustrated at the very distal end of the instrument shaft. A push-pull cable 164 extends through the instrument shaft 162 and is secured at a rotational barrel 166 within the slider 168. End effector actuation occurs via the lever 167. The view of FIG. 19 illustrates the instrument having been inserted into the guide member. At the proximal end of the assembly, there are provided one bendable member 20 of the guide member, a rotation knob and grip on the guide member and and a rotation knob 156 of the instrument handle. At the distal end of the instrument, there is provided distal bendable member 22 of the guide member. The embodiment of FIGS. 18 and 19 allows bending at the proximal bendable member and also allows rotation at the knob 156. The catch 176 in the annular slot 172 of coupler 170 prevents any linear translation of the instrument relative to the guide member but permits relative rotation of the instrument handle. The 170 is adapted to fit within the cinical cavity 174 of the guide member.

In the embodiment of FIGS. 18 and 19 there are several degrees of motion that are possibly due to the bendable members that are used and the rotations that are possible. Some of these motion are illustrated in FIG. 19 by means of corresponding arrows. Arrow 171 indicates a rotation of the instrument and arrow 173 indicates a corresponding rotation at the instrument end effector. Arrow 175 indicates a rotation of the guide member at the grip 142 and arrow 177 indicates a corresponding rotation at the distal end of the guide member. Arrow 179 indicates a bending at the bendable section 20 and arrow 181 indicates a corresponding bending at the distal bendable member 22.

Reference is now made to related application Ser. Nos. 10/822,081 filed Apr. 12, 2004 and 11/185,911 filed Jul. 20, 2005 which are hereby incorporated by reference herein and considered as a part of the disclosure in the instant application. The subject matter of these applications incorporates proximal and distal bendable members within the instrument itself. An instrument of this type can also be used in association with the guide member of the present invention that also includes proximal and distal bendable sections or members. Embodiments are now described that incorporate bendable members in both the instrument and guide member.

A seventh embodiment is shown in FIGS. 20 and 21. This embodiment employs a non-conventional instrument such as the instrument described in co-pending application Ser. No. 11/185,911, filed Jul. 20, 2005 which uses proximal and distal bendable sections of the instrument. Thus, the combined assembly actually has two proximal bendable members and two distal bendable members so as to provide greater degrees of control of the end effector. There is a proximal bendable member on the guide member and one on the instrument itself. There is a distal bendable member on the guide member and one on the instrument itself.

FIG. 20 is an exploded side view of the fifth embodiment of the guide device as used with a fifth embodiment of the surgical instrument. FIG. 21 is a schematic side view of the instrument and guide assembly of FIG. 20 in use as inserted through a patient's skin at an incision. The embodiment of FIGS. 20 and 21 differs from the embodiment of FIGS. 18 and 19 primarily in that it has the ability to linearly translate the instrument within the guide member. FIG. 21 shows the various motions of the assembly as illustrated by the arrows.

Accordingly, in the embodiment of FIGS. 20 and 21 there is provided an instrument that has a rotation knob 182 with a boss 184 that extends within a cavity 186 of the handle 40. FIG. 20 also illustrates the instrument shaft 162, the proximal bendable member 188 and the distal bendable member 190. An end effector 38 is also illustrated at the very distal end of the instrument shaft. A push-pull cable 164 extends through the instrument shaft 162 and is secured at a rotational barrel 166 within the slider 168. For further details of the instrument described in FIG. 20, refer to application Ser. Nos. 10/822,081 and 11/185,911 and, in particular, FIG. 8 of Ser. No. 11/185,911.

The embodiment in FIGS. 20 and 21 also includes the grip portion 142 and the rotation knob 144 that have been described previously in connection with FIGS. 15-17. In FIG. 20 the guide member 140 also includes proximal bendable member 20, distal bendable member 22 and guide shaft 18. The coupler 26 connects the proximal bendable member with the guide shaft.

The view of FIG. 21 illustrates the instrument having been inserted into the guide member. At the proximal end of the assembly, there are provided two bendable members, namely, proximal bendable members 20 and 188, associated, respectively, with the grip 142 and the instrument handle 40. At the distal end of the instrument, there are provided distal bendable members 22 and 190 associated, respectively, with the guide shaft 18 and the instrument shaft 162. The version of FIG. 21 also can provide linear translation of the instrument within the guide. The arrows in FIG. 21 show the various motions.

In the embodiment of FIGS. 20 and 21 there are several degrees of motion that are possibly due to the several bendable members that are used and the rotations that are possible. Some of these motion are illustrated in FIG. 21 by means of corresponding arrows. Arrow 171 indicates a rotation of the instrument at the knob 182 and arrow 173 indicates a corresponding rotation at the instrument end effector. Arrow 175 indicates a rotation of the guide member at the grip 142 and arrow 177 indicates a corresponding rotation at the distal end of the guide member. Arrow 179 indicates a bending at the bendable section 20 and arrow 181 indicates a corresponding bending at the distal bendable member 22. Arrow 183 indicates a bending at the bendable section 188 and arrow 185 indicates a corresponding bending at the distal bendable member 190.

An eighth embodiment of the invention is illustrated in FIGS. 22 and 23. This embodiment is quite similar to the embodiment illustrated in FIGS. 20 and 21 in that it uses the two pairs of cooperating bendable sections, one pair on the instrument and the other pair on the guide member. However, in this embodiment a one-piece grip portion is employed with a catch 176 for securing the instrument within the grip portion, while allowing rotation, but no linear translation. Refer to FIGS. 12-14 for further details of the grip portion of the guide member.

FIG. 22 is an exploded side view of the sixth embodiment of the guide device as used with a sixth embodiment of the surgical instrument. FIG. 23 is a schematic side view of the instrument and guide assembly of FIG. 22 in use as inserted through a patient's skin at an incision. In FIG. 22 the guide member 142 has a conical cavity 174 into which the catch 176 can extend for engagement with the instrument body. This engagement allows relative rotation but not linear translation.

Accordingly, in the embodiment of FIGS. 22 and 23 there is provided an instrument 194 that has a rotation knob 182 with a boss 184 that extends within a cavity 186 of the handle 40. FIG. 22 also illustrates the instrument shaft 162, the proximal bendable member 188 and the distal bendable member 190. An end effector 38 is also illustrated at the very distal end of the instrument shaft. A push-pull cable 164 extends through the instrument shaft 162 and is secured at a rotational barrel 166 within the slider 168. For further details of the instrument described in FIG. 22, refer to application Ser. Nos. 10/822,081 and 11/185,911 and, in particular, FIG. 8 of Ser. No. 11/185,911.

The embodiment in FIGS. 22 and 23 also includes an instrument having a cover or coupler 192 that connects the proximal bendable member 188 with the guide shaft 162. The coupler 192 has an annular groove 196 that is adapted to receive the free end of the catch 176. This catch and groove arrangement allows rotation between the instrument and the guide member. The conical surface of the coupler 192 mates with the conical shaped cavity 174 in the grip 142. FIG. 23 shows the instrument fully and operably engaged with the guide member.

In the embodiment of FIGS. 22 and 23 there are several degrees of motion that are possibly due to the several bendable members that are used and the rotations that are possible. Some of these motion are illustrated in FIG. 23 by means of corresponding arrows. Arrow 171 indicates a rotation of the instrument at the knob 182 and arrow 173 indicates a corresponding rotation at the instrument end effector. Arrow 175 indicates a rotation of the guide member at the grip 142 and arrow 177 indicates a corresponding rotation at the distal end of the guide member. Arrow 179 indicates a bending at the bendable section 20 and arrow 181 indicates a corresponding bending at the distal bendable member 22. Arrow 183 indicates a bending at the bendable section 188 and arrow 185 indicates a corresponding bending at the distal bendable member 190.

Figure 24:
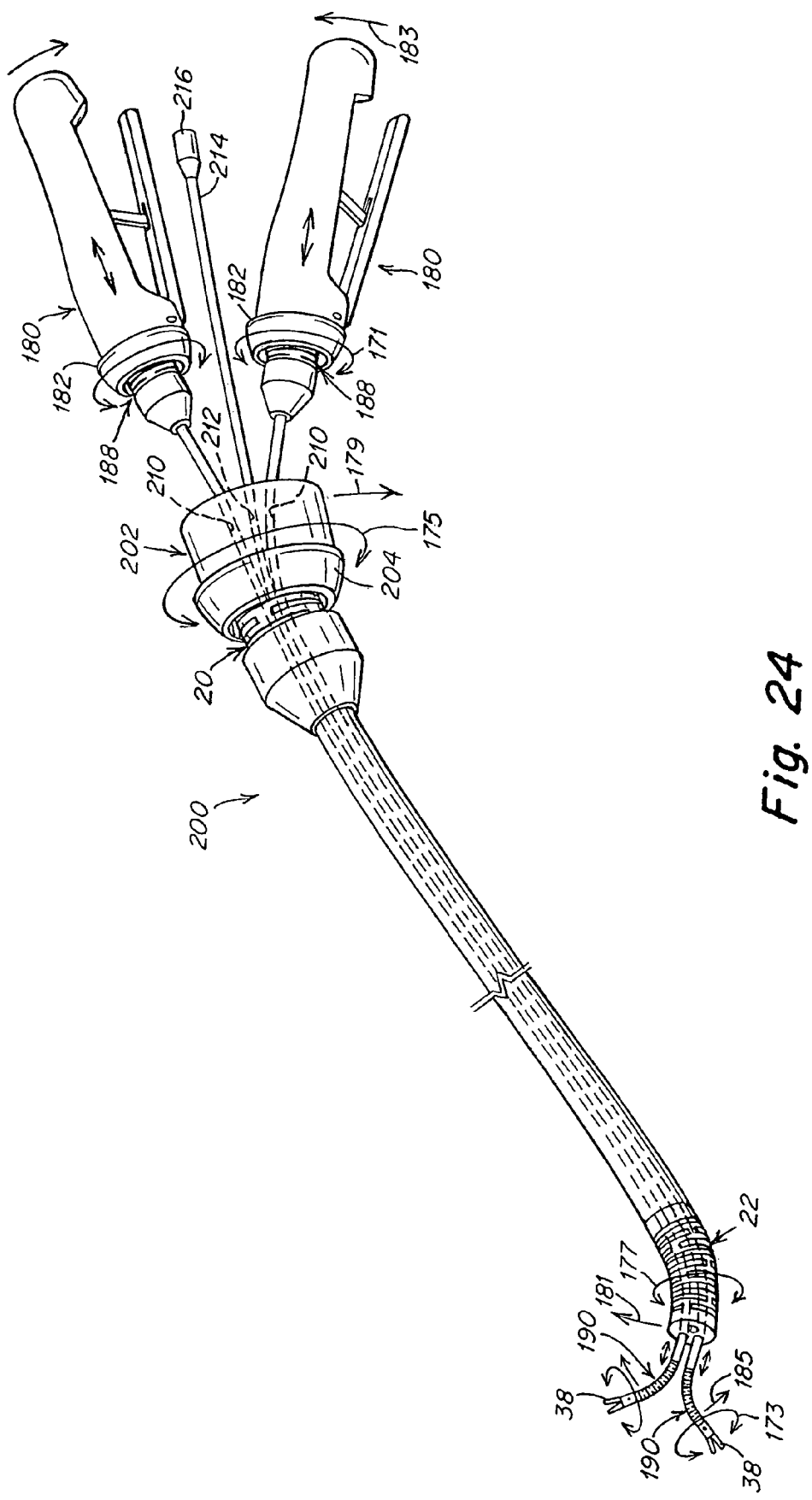
FIG. 24 is a perspective view of another embodiment of the guide device useable with two or more instruments.

A nineth embodiment of the present invention is shown in FIG. 24 in which the guide member accommodates multiple instruments as well as other possible instrumentation. Any of the various instruments that have been previously illustrated may be used in this embodiment. FIG. 24 shows a channel that may be used, for example, for irrigation purposes or for optics. FIG. 24 is an embodiment in which the guide shaft has multiple channels for receiving multiple instruments or other devices and may be either flexible, rigid or semi-flexible. FIG. 24 shows a connector 216 coupled to a proximal end of a catheter or other tubular device 214 that can be used either for optics or for other purposes. The tube 214 extends through one of the lumens within the guide member 200. Both of the instruments illustrated in FIG. 24 may be considered as of the same type as previously described in either FIG. 20 or 22. Each of these instruments is illustrated as controling a respective end effector 38.

In the embodiment of FIG. 24 there is provided a one-piece grip 202 having a raised lip 204 that may be grasped by the user. In an alternate embodiment a two-piece grip may be used. The guide member has a proximal bendable member 206 and a distal bendable member 208. Cabling connects between these bendable members in the same manner as previously described with guide members having only one lumen. The guide member 200 may be considered as having three separate lumens; two lumens 210 accommodate the respective instruments 180 and one lumen 212 is for receiving the catheter, tube or shaft 214. In this embodiment because the instruments have been described before there is no detailed description herein. Refer to FIGS. 19-23. Each of the instruments includes a proximal bendable section 188 and a distal bendable section 190. Each also includes a control knob 182.

In the embodiment of FIG. 24 there are several degrees of motion that are possible due to the several bendable members that are used and the rotations that are possible. Some of these motion are illustrated in FIG. 24 by means of corresponding arrows. Arrow 171 indicates a rotation of the instrument at the knob 182 and arrow 173 indicates a corresponding rotation at the instrument end effector. Arrow 175 indicates a rotation of the guide member at the grip 142 and arrow 177 indicates a corresponding rotation at the distal end of the guide member. Arrow 179 indicates a bending at the bendable section 20 and arrow 181 indicates a corresponding bending at the distal bendable member 22. Arrow 183 indicates a bending at the bendable section 188 and arrow 185 indicates a corresponding bending at the distal bendable member 190.

Figure 25:
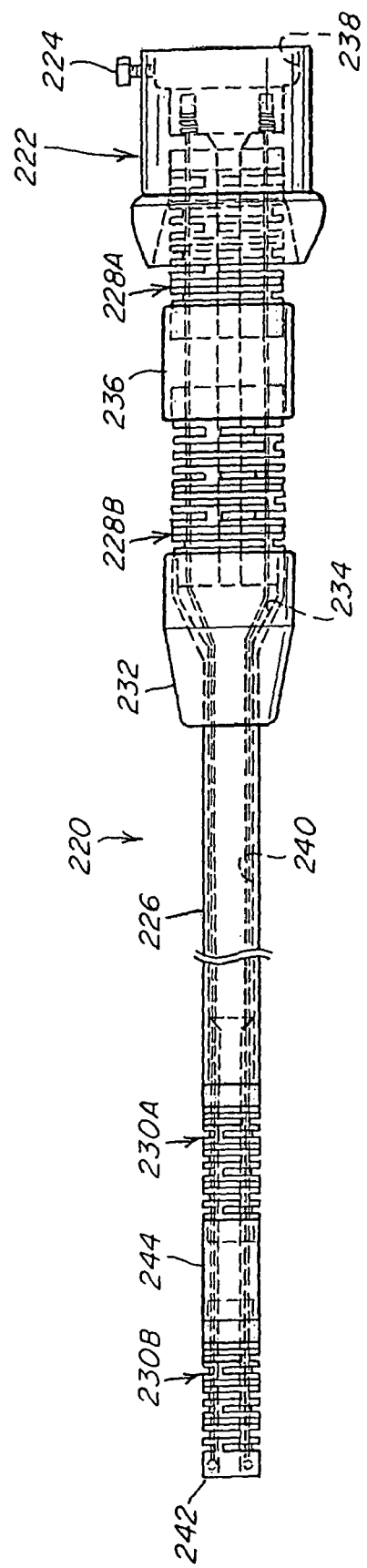
FIG. 25 is a side view of still another embodiment of the invention using multiple bendable members both proximally and distally on the guide member.

Reference is now made to a further embodiment of the present invention illustrated in FIG. 25 in which the guide member accepts one or more instruments, but instead of having a single bendable member on each end of the guide shaft there are two or more bendable members or sections on each end. A first proximal bendable member controls a first distal bendable member and a second proximal bendable member controls a second distal bendable member. The control is by means of first cabling that extends between the respective first bendable members and separate second cabling that extends between the respective second bendable members. In this way, an instrument inserted in the guide member has enhanced control by virtue of added degrees of control with the multiple proximal bendable members controlling respective multiple distal bendable members.

FIG. 25 shows an instrument guide member that incorporates the multiple bendable member concepts. This guide member 220 may be similar to that described previously in FIG. 1 but includes multiple bendable sections at both ends of the guide member. Although only two bendable members are illustrated at each end of the guide member, it is understood that more than two may be incorporated in the guide device 220. The guide member 220 may receive an instrument such as the instrument disclosed in FIG. 1, but can also receive other instrument designs such as other ones disclosed herein or in the related application mentioned herein. The particular instrument of FIG. 1 locks to the grip portion 222 of the guide member 220 by means of the locking screw 224. An end effector (not shown) extends from the very distal end of the guide member 220 when the instrument is fully inserted in the guide member. The guide of FIG. 25 may also accommodate multiple instruments, as in FIG. 24.

In FIG. 25, the guide member or guide instrument 220 is depicted separately from the surgical instrument as in FIG. 1. The assembled system has the instrument inserted into and through the guide member 220. The guide member 220 includes a guide shaft 226 that may extend through a cannula at an insertion site of the patient disposing the proximal bendable members outside the patient and the distal bendable members within the patient adjacent the operative site. The end effector or tool extends from the very distal end of the guide member. A protective sheath may extend about one or both of the distal flexible or bendable members.

The guide member 220, in addition to including the guide shaft 226, also includes a first proximal flexible or bendable member 228A and a second proximal flexible or bendable member 228B. An adaptor cover 232 is disposed about a portion of the proximal bendable member 228B. The adaptor cover 232 includes a funnel or conical-shaped portion or cavity 234 (see cavity 96 in FIG. 6) for respectively receiving ends of the proximal bendable member 228B and the guide shaft 226. The more proximal end of the proximal bendable member 228B is held in an intermediate member 236 that may be of various lengths depending upon the particular medical application. The intermediate section 236 may be rigid, flexible or semi-flexible, but is preferably rigid. The intermediate member 236 also holds the more distal end of the proximal bendable member 228A. The bendable members 228A and 228B are thus separately mounted and can be separately controlled from the instrument handle actions.

The grip 222 of the guide member 220 receives the other end of the proximal bendable member 228A. The grip 222 is preferably a single piece structure having a cavity 238 for receiving the boss of the instrument, as depicted in FIG. 1. The boss may also be provided with a recess for receiving the locking screw 224 that extends through the grip 222 into the cavity 238 and into the recess in the instrument. The use of the locking screw 224 secures the instrument within the guide member 222. Motions of the instrument are thus directly transferred to the grip 222 and both of the proximal bendable members. The length of the guide member is selected so that the instrument tool extends beyond the end of the guide member, as depicted in FIG. 3.

The embodiment of FIG. 25 also discloses the details of the proximal and distal bendable members 228 and 230. Each of the members may be constructed as illustarted before in FIGS. 4-6. All of these bendable member have a central passage through which the instrument shaft can extend. FIG. 25 also illustrates the lumen 240 defined by the guide shaft 226 with the instrument shaft extendable therethrough. Similarly, the distal bendable members include a centrally disposed passage for receiving the more distal end of the instrument shaft. In FIG. 25 the guide shaft 226 is shown as rigid, but could also be partially flexible or flexible. The guide shaft 226 may be made of a light weight metal material or of plastic.

The grip 222 includes a cavity (see FIG. 6) for receiving one end of the proximal bendable member 228A. The grip 222 also preferably includes a raised lip that is useful in grasping the guide grip 222. The raised lip preferably has spaced finger grooves. This bendable member 228A is seated at an end wall of the grip 222. This end wall may have a tapered or conical passage for receiving the instrument shaft. As depicted in FIG. 6, there are also provided several passages for cabling. The grip 222 may also include a cavity for anchors and springs, as depicted in the first embodiment described herein. This includes a plurality of proximal anchors and related springs. The springs are for tensioning the associated cables. For the proximal bendable member 228B the anchors and springs may be disposed in the intermediate member 236. Cabling associated with the proximal bendable member 228A passes through the intermediate member 236.

The guide member 220, at the distal end thereof, includes a pair of spacedly disposed distal bendable members 230A and 230B separated by the intermediate member 244. The distal bendable members 230A and 230B may include an extending end 242 for receiving distal anchors that secure the distal ends of the actuation cables. The actuation cables associated with the distal bendable member 230A may be disposed in the intermediate section 244 between the distal bendable members 230A, 230B. The control between the proximal and distal bendable members is carried out primarily by means of a set of cables that extend between these bendable members. A bending at the proximal bendable member causes a pulling of one or more cables while there is a relaxing of other opposed cables causing a corresponding bending action at the distal bendable member. The cabling may be provided in either the arragement of FIG. 7 or of FIG. 8, depending on the desired direction of bending.

The cabling that is used includes flexible cables that extend between the proximal and distal bendable members. Refer to FIG. 1. A plurality of distal anchors are used at each end of the cabling. Cable passages are provided in the proximal bendable members and the distal bendable members. The passages accommodate these cables. Also, guide discs (not shown) may be provided along the cables, particularly within the guide shaft so as to assure that the cables are maintained in position as they extend from one end of the guide shaft to the other end.

The proximal bendable members are each comprised of a series of adjacent discs that define therebetween spaces or slots, as in FIGS. 4-6. Connecting ribs extend between adjacent discs. FIG. 5 depicts the location of the ribs. In a similar manner, the distal bendable members each include a series of discs that define therebetween slots or spaces. Ribs extend between adjacent discs. For further details of the bendable members and the preferred relationship between the disks, slots and ribs, refer to application Ser. No. 11/185,911, filed on Jul. 20, 2005, the content of which is hereby incorporated by reference herein.

Now, in the embodiment of FIG. 25 the cabling is preferably connected so that there are four cables between the proximal bendable member 228A and the distal bendable member 230B, and likewise there are four cables between the proximal bendable member 228B and the distal bendable member 230A. In an alternate arrangement the cabling from the proximal bendable member 228A may control the distal bendable member 230A and the cabling from the proximal bendable member 228B may control the distal bendable member 230B. Also, fewer or greater numbers of cables may be used for control between the proximal and distal bendable members.

The user of the instrument system may grasp the instrument handle, engage the instrument with the guide, as in FIG. 3 and manipulate the guide member essentially by manipulating the instrument handle which is secured to the guide grip 222. A deflection, for example, of the proximal bendable member 228A causes the cables to be tensioned and relaxed so as to cause the distal bendable member 230B to be correspondingly deflected. This deflection may be in the same direction or in opposed directions. See FIGS. 7 and 8. Similarly, a deflection of the proximal bendable member 228B causes the cables to be tensioned and relaxed so as to cause the distal bendable member 230A to be correspondingly deflected.

Figure 26:
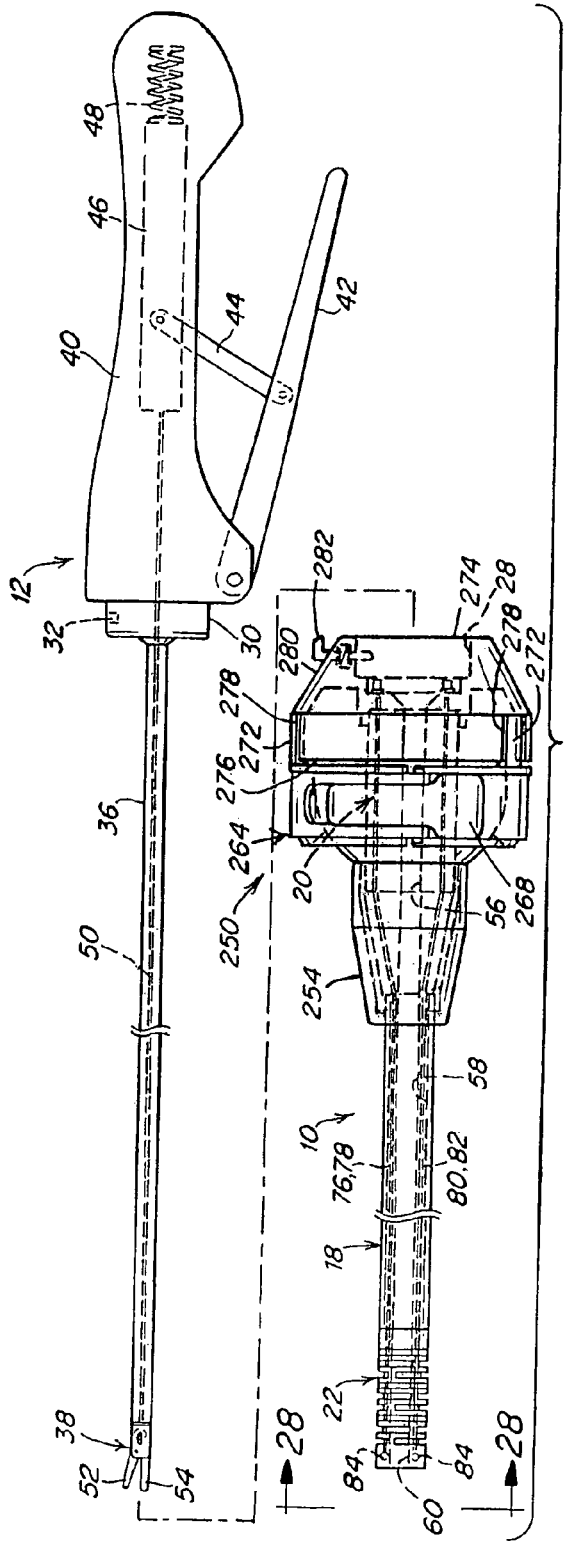
FIG. 26 is an exploded side view of another embodiment of the manual instrument and guide member and including a locking feature.
Figure 27:
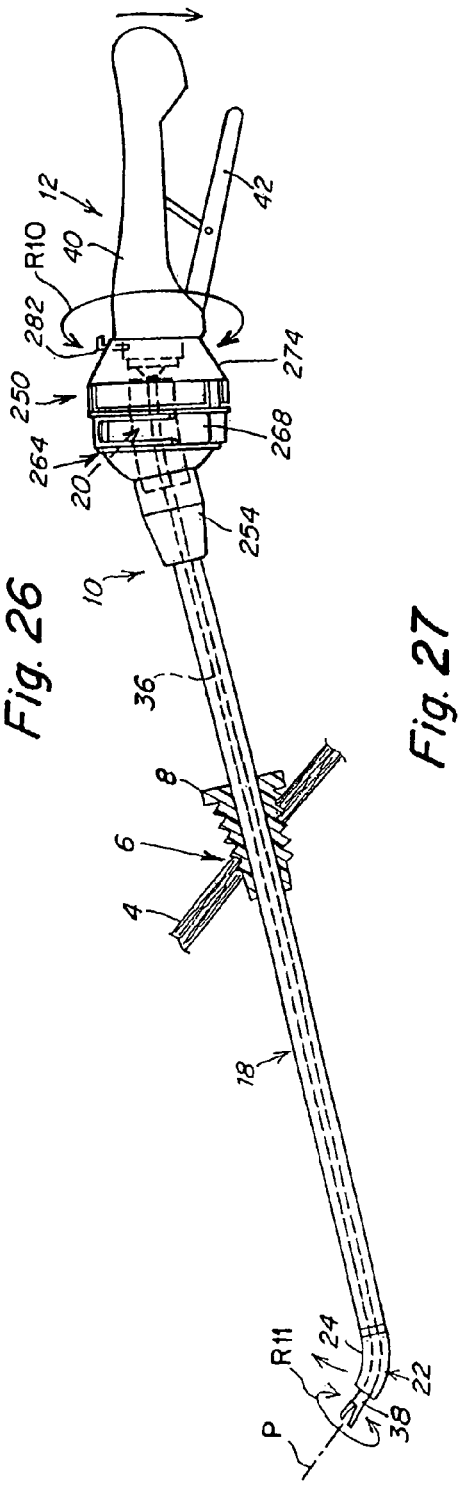
FIG. 27 is a schematic side view of the instrument of FIG. 26 and in use.
Figure 30:
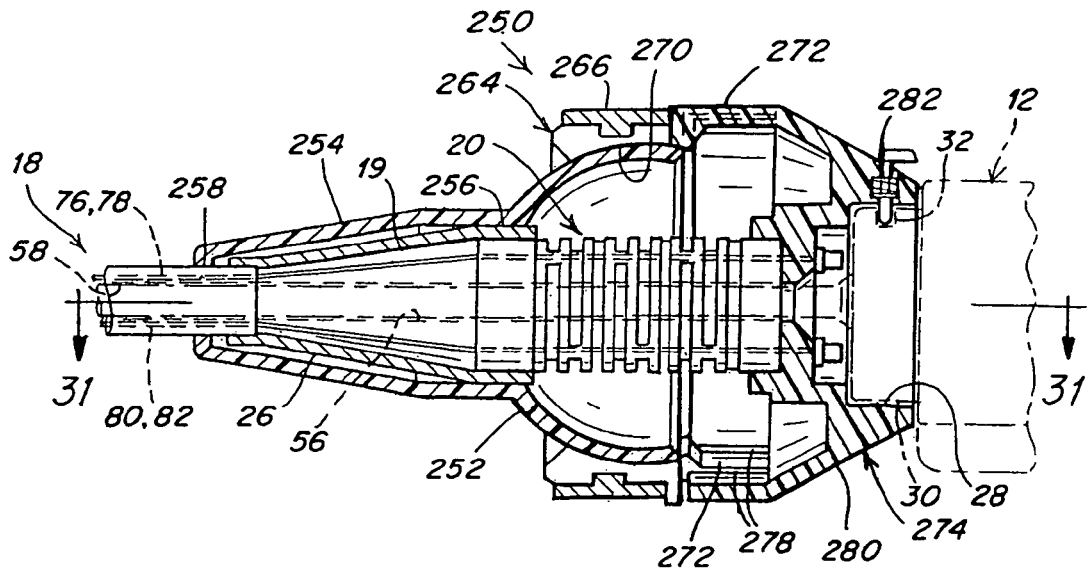
FIG. 30 is a cross-sectional side view of the angle locking means shown in FIGS. 26-29.
Figure 31:
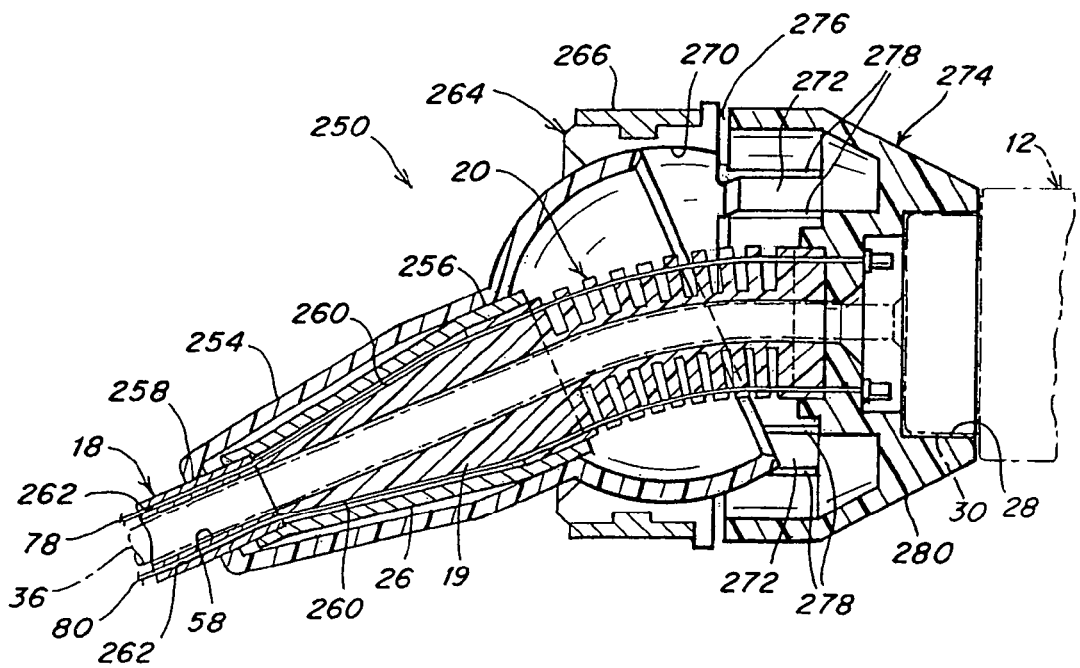
FIG. 31 is a cross-sectional side view like that shown in FIG. 30, but with the angle locking means engaged.

Reference is now made to a further embodiment of the present invention in which a locking feature is added to the guide member. In this regard see this embodiment illustrated in FIGS. 26-31. FIG. 26 is an exploded side view of still another embodiment having a locking feature. FIG. 27 is a schematic side view of the instrument of FIG. 26 and in use. FIG. 28 is an end view as taken along line 28-28 of FIG. 26. FIG. 29 is a partially exploded perspective view of the manually operated instrument being inserted into the guide member. FIG. 30 is a cross-sectional side view of the angle locking means shown in FIGS. 26-29. FIG. 31 is a cross-sectional side view like that shown in FIG. 30, but with the angle locking means engaged.

In FIGS. 26-31 the guide member or instrument 10 has a proximal bendable member 20 and distal bendable member 22 and receives, via lumen 58, the manually operated instrument 12 such as depicted in FIG. 27 in the inserted position of the instrument 12. The instrument 12 may be conventional and is secured in the guide member 10 so that motions at the instrument handle 40 are essentially transferred through the guide member 10 to control the positioning of the end effector or tool. In other words a deflection of the handle 40 causes a bending of the proximal bendable member 20 which, in turn, bends the distal bendable member 22 to control the placement of the tool or end effector 38 of the manually operated instrument. This embodiment also includes a grip portion 274 that provides the interface between the handle 40 and the proximal bendable member 20. In this embodiment there is no rotation knob provided. The instrument 12 is locked to the guide member 10 so there is also no linear motion of the instrument relative to the guide member.

Referring to FIG. 27, the surgical instrument 12 may be considered as of conventional design and is comprised of a handle 40 at the proximal end of the instrument, an elongated flexible instrument shaft 36 and a tool or end effector 38 disposed at the distal end of the surgical instrument 12. In the disclosed embodiment the instrument shaft 36 is preferably constructed so as to be at least partially flexible or bendable so as to sufficiently bend with the bending of the bendable members of the guide member 10. At the least the instrument shaft is flexible at the area corresponding to the two bendable sections, but could be rigid at other area along its length. The tool 38 is illustrated as including a fixed jaw 54 and a moveable jaw 52. The tool 38 is actuated by means of an actuation cable 50 that extends through the instrument shaft 36 and is controlled from the slider 46 and return spring 48. The slider and return spring are shown in dotted outline in FIG. 26. A lever 42 operates the slider 46 through the linkage or transfer bar 44. The closure of the lever 42 pulls the cable 50 to close the jaws 52, 54. For further details of the tool actuation mechanism refer to co-pending application Ser. No. 11/185, 911, filed on Jul. 20, 2005, the content of which is hereby incorporated by reference herein.

In FIG. 26 the guide member or guide instrument 10 is depicted separately from the manually operated surgical instrument 12. In FIG. 27, there is shown the assembled system with the instrument having been inserted into and through the lumen 58 of the guide member 10. In FIG. 27 note that the guide member shaft 18 extends through the cannula 8 at the insertion site 6 of the patient's skin 4. The end effector or tool 38 is disclosed in FIG. 27 as extending from the distal bendable member 22. FIG. 27 also shows a protective sheath 24 that may extend about the distal flex member 22.

The guide member 10, in addition to including the guide shaft 18, also includes the proximal flexible or bendable member 20 and the distal flexable or bendable member 22. An adaptor cover 26 is disposed about a portion of the proximal bendable member 20. The adaptor cover 26 includes a funnel or conical-shaped portion for receiving ends of the proximal bendable member 20 and the guide shaft 18.

The manual instrument 12 is illustrated as having an end boss 30 that is provided with a recess 32 for receiving a spring loaded latch 282 that extends into the recess 32 in the instrument boss 30. The use of the spring loaded latch 282 secures the instrument 12 within the guide member 10. The latch 282 is supported by the hub or grip portion 274, as shown in FIG. 30. Motions of the instrument 12 are thus directly transferred to the hub 274 and, in turn, to the proximal bendable member 20. Thus, a user can insert the manual instrument in the guide member, and then control the distal part of the manual instrument by moving or deflecting the handle 40 such as to a position illustrated in FIG. 31. The relative length of the guide member and instrument are selected so that the instrument tool extends beyond the end of the guide member, as depicted in FIG. 27.

In FIGS. 26-31 there is shown some details of the proximal and distal bendable members 20 and 22. Bendable member 20 has a central passage through which the instrument shaft 36 can extend. In this regard the lumen 58 defined in the guide shaft 18 may be considered as extending also through both bendable members. Thus, the distal bendable member 22 also includes a passage for receiving the instrument shaft 36. The guide shaft 18 may be rigid, partially rigid or flexible. The guide shaft 18 may be made of a light weight metal material or of plastic.

The bendable member 20 is seated at its proximal end in the grip portion 274. An end wall receives the ends of cabling at anchors and possible associated springs. This includes a plurality of proximal anchors and related springs. The springs are for tensioning the associated cables 76-82. The distal bendable member 22 includes an extending end for receiving the distal anchors 84 that secure the distal ends of the actuation cables 76-82.

The control between the proximal and distal bendable members is carried out primarily by means of a set of cables that extend between these bendable members. A bending at the proximal bendable member causes a pulling of one or more cables while there is a relaxing of other opposed cables causing a corresponding bending action at the distal bendable member. The cabling that is used includes flexible cables 76, 78, 80 and 82 that extend between the proximal and distal bendable members. A plurality of distal anchors 84 are used at the distal end of the cabling. Cable passages are provided in the proximal bendable member 20, and cable passages are provided in the distal bendable member 22. The passages accommodate these cables. Also, guide discs (not shown) may be provided along the cables, particularly within the guide shaft 18 so assure that the cables are maintined in position as they extend from one end of the guide shaft to the other end.

The proximal bendable member 20 is comprised of a series of adjacent discs that define therebetween spaces or slots. Connecting ribs may extend between adjacent discs. In a similar manner, the distal bendable member 22 includes a series of discs that define therebetween slots or spaces. Ribs may extend between adjacent discs. For further details of the bendable members and the prefered relationship between the disks, slots and ribs, refer to application Ser. No. 11/185,911, filed on Jul. 20, 2005, the content of which is hereby incorporated by reference herein.

The angle locking means 250 allows the instrument user to hold a particular position and orientation of the guide member and, in turn, the instrument itself. The locking member comprises an angle locking means 250 that includes a ball and socket arrangement that is compressed by an outer cinch ring member. The locking mechanism or angle locking means 250 includes a ball and socket arrangement that is disposed over the proximal bendable member 20 and that follows the bending at the proximal bendable member. The locking mechanism has locked and unlocked positions, is disposed about the proximal movable or bendable member and is manually controlled from the manually operated instrument 12 so as to fix the position of the proximal movable member relative to the handle 12 in the locked position thereof. The locking mechanism comprises a ball member and a compressible hub that defines a socket member. in the disclosed embodiment the hub is a split hub and the locking mechanism further includes a cinch ring disposed about the split hub and a locking lever mounted on the cinch ring for closing the cinch ring about the hub to lock the hub against the spherical ball member. The cinch ring interlocks with the hub but is preferably able to rotate relative thereto when in the unlocked position.

The "ball" part is basically formed by the ball member 252, while the "socket" part is basically formed by an extension of the handle, namely the split hub 264, and identified in the drawings by the socket 270, such as is illustrated in FIG. 31. The locking mechanism locks the proximal bendable member in a desired position and by doing that also locks the position of the distal bendable member 22 of the guide and tool 38 of the manually operated instrument 10. The proximal bending member 20, although it is enclosed by the ball and socket arrangement, still allows the instrument shaft 18 and the proximal bending member 20, along with the cabling 76, 78, 80, 82, to rotate freely while also allowing the axis of the instrument shaft 36 to be angled relative to the axis of the handle in a free, or alternately, locked mode.

For this purpose refer to the ball member 252 which is shown in further detail in FIGS. 30 and 31. The ball member 252 includes a distal neck 254 that is contiguous with a partially spherical ball end having a partially spherical outer surface. The neck 254 is basically disposed over the adaptor 26 and conical portion 19 of the proximal bendable member 20, while the ball 252 portion is mainly disposed over the primary part of the proximal bendable member 20. The ball member 252 is adapted to sit within a socket 270 that is formed in the handle in the form of the split hub 264 that can be collapsed about the ball member 252 by radially compressing the cinch ring 266.

The ball member 252 is gimbaled in the split hub 264 that is comprised of four quadrants or petals 264A-264D that can be clamped against the outer spherical surface of the ball member 252 by means of the cinch ring 266. The split hub 264 is supported at the distal end of the handle by means of a plurality of spacedly disposed struts 272 that, in one embodiment, are spaced approximately 120 degrees apart. The struts are supported from the proximal hub 274, as shown in FIG. 30. As mentioned previously, the ball member 252 has a neck portion 254 that provides support for the distal end of the proximal bendable member 20.

FIGS. 28 and 29 illustrate the cinch ring 266. Refer also to FIGS. 30 and 31 for an illustration of the cinch ring 266. The cinch ring 266 is an annular member that may be provided with an internal ridge or spline that is adapted to mate with a channel or groove in the outer surface of the split hub. This combination of a channel and ridge limits the annular cinch member to just rotation about the hub. FIG. 28 shows that each of the portions 264A-264D of the split hub connects to the instrument handle via respective struts 272 (see also FIGS. 29 and 30). When the cinch ring 266 is closed this, in turn, closes the slotted hub and essentially compresses the socket 270 against the outer spherical surface of the ball member 252. The locking of the ball member thus fixes the position of the proximal bendable member 20, and, in turn, the distal bendable member 22 and tool 38. For further details of the ball and socket arrangement and associated cinch ring construction refer to co-pending application Ser. No. 11/649,352 filed on Jan. 2, 2007, the entire contents of which is hereby incorporated by reference.

The cinch ring 266 is operated by means of an over-center locking lever 268 that is connected to ends of the cinch ring 266 by means of the pins or the like. FIG. 28 illustrates the lock lever 268 in a locked position while FIG. 29 illustrates the lock lever in a released or unlocked position. The cinch ring 266 is free to rotate around the split hub when lever 268 is released by means of the spline that rides in the groove in the circumference of the split hub. This allows for left or right handed operation of the instrument.

When the locking lever 268 is moved to its locked position this compresses the cinch ring 266 closing the hub against the spherical outer surface of the ball member 252. This locks the hub 274 against the ball member 252 holding the ball member in whatever position it is in when the locking occurs. By holding the ball member in a fixed position this, likewise, holds the proximal bendable member in a particular position and fixed in that position. This, in turn, maintains the distal bendable member and tool at a fixed position.

In the embodiment of FIGS. 26-31 because the handle is locked with the guide member by means of the latch 282, when the handle is rotated in the direction of the arrow R10 then the end effector 38 actually orbits in and out of the plane of the paper in FIG. 27. The rotation of the handle provides rotation of the guide shaft, as well as the instrument shaft, but this is transferred to the tip of the instrument by orbiting the end effector. If the latch 282 is constructed so that it is releasable, then the manual instrument may be rotated separately from the guide member. In that case, if the guide member is held stationary (but in a bent condition, for example, per FIG. 27) when the manual instrument is rotated, such as in the direction of arrow R10 in FIG. 27, then the end tool 38 rotates about the distal tool axis (arrow R11) represented in FIG. 27 by the axis P.

Figure 34:
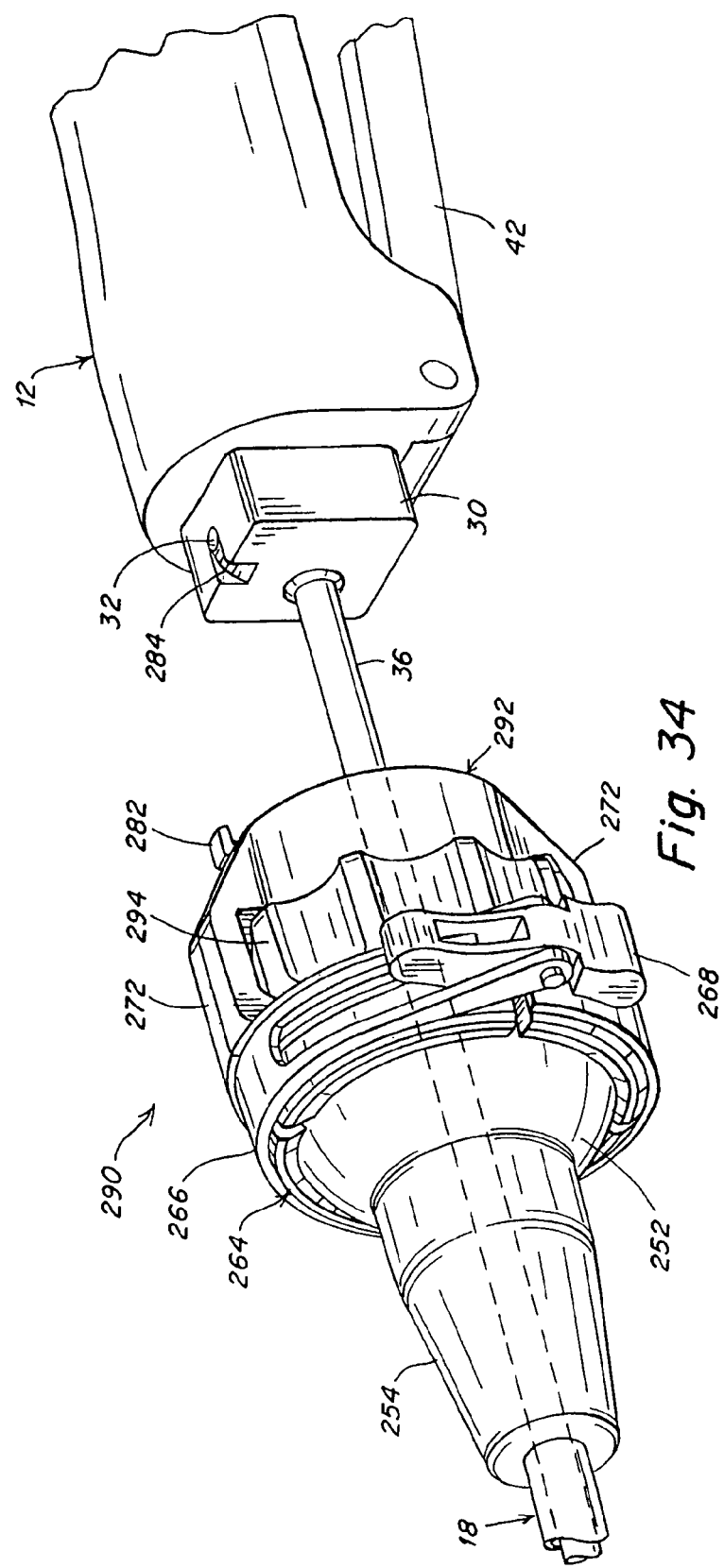
FIG. 34 is a partially exploded perspective view of the manually operated instrument being inserted into the guide member.
Figure 35:
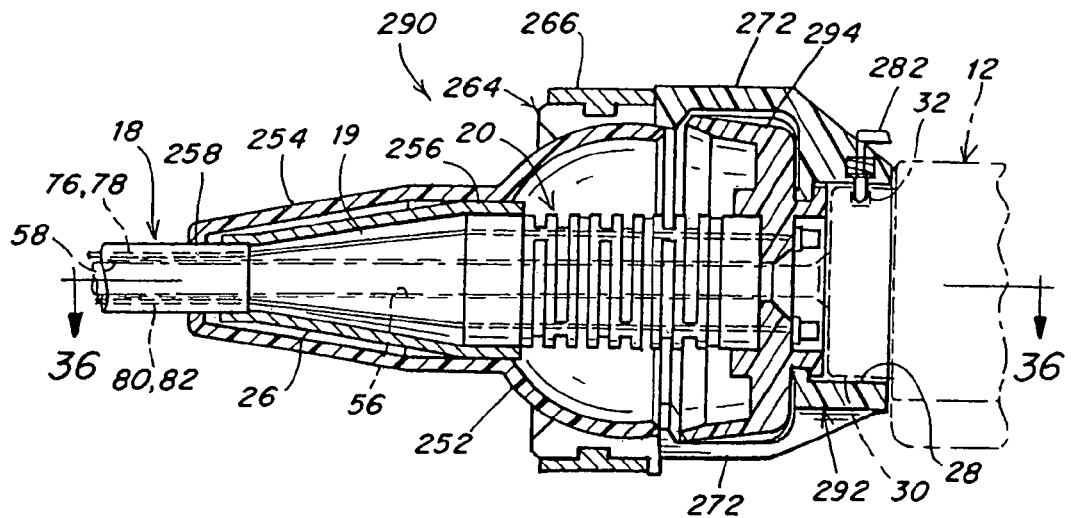
FIG. 35 is a cross-sectional side view of the angle locking means shown in FIGS. 32-34.
Figure 36:
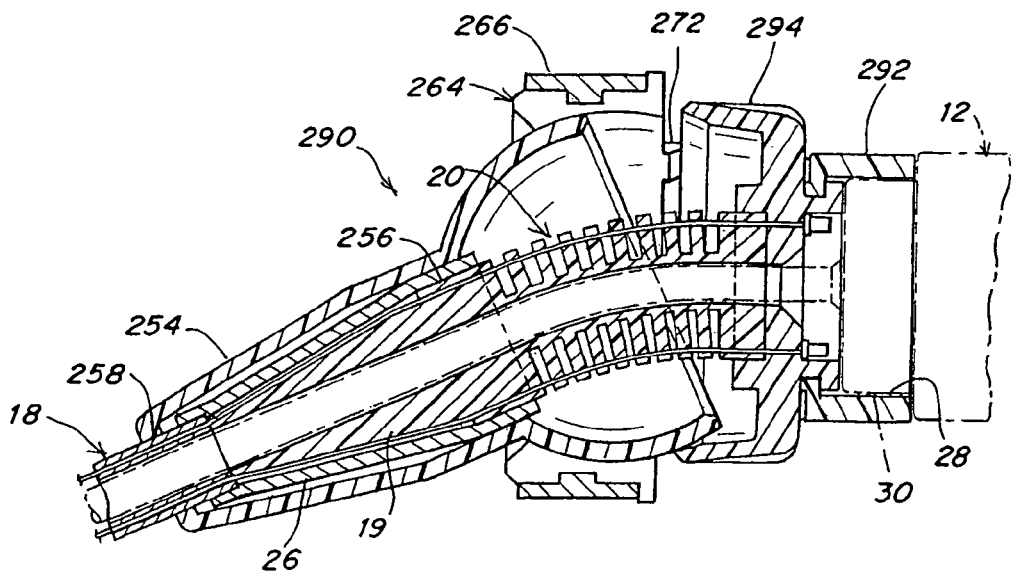
FIG. 36 is a cross-sectional side view like that shown in FIG. 35, but with the angle locking means engaged.

Reference is now made to a further embodiment of the present invention in which a locking feature is added to the guide member. In this regard see this embodiment illustrated in FIGS. 32-36. FIG. 32 is an exploded side view of still another embodiment having a locking feature. FIG. 33 is a schematic side view of the instrument of FIG. 32 and in use. FIG. 34 is a partially exploded perspective view of the manually operated instrument being inserted into the guide member. FIG. 35 is a cross-sectional side view of the angle locking means shown in FIGS. 32-34. FIG. 36 is a cross-sectional side view like that shown in FIG. 35, but with the angle locking means engaged.

In FIGS. 32-36 the guide member or instrument 10 has a proximal bendable member 20 and distal bendable member 22 and receives, via lumen 58, the manually operated instrument 12 such as depicted in FIG. 33 in the inserted position of the instrument 12. The instrument 12 may be conventional and is secured in the guide member 10 so that motions at the instrument handle 40 are essentially transferred through the guide member 10 to control the positioning of the end effector or tool. In other words a deflection of the handle 40 causes a bending of the proximal bendable member 20 (as in FIG. 33) which, in turn, bends the distal bendable member 22 to control the placement of the tool or end effector 38 of the manually operated instrument . This embodiment also includes a grip portion 292 that provides the interface between the handle 40 and the proximal bendable member 20. The guide member 10 also includes a rotation knob 294 for controlling the rotation of the bendable members and tool. The instrument 12 is locked to the guide member 10 so there is no linear motion of the instrument relative to the guide member.

Referring to FIG. 33, the surgical instrument 12 may be considered as of conventional design and is comprised of a handle 40 at the proximal end of the instrument, an elongated flexible instrument shaft 36 and a tool or end effector 38 disposed at the distal end of the surgical instrument 12. In the disclosed embodiment the instrument shaft 36 is preferably constructed so as to be at least partially flexible or bendable so as to sufficiently bend with the bending of the bendable members of the guide member 10. The tool 38 is illustrated as including a fixed jaw 54 and a moveable jaw 52. The tool 38 is actuated by means of an actuation cable 50 that extends through the instrument shaft 36 and is controlled from the slider 46 and return spring 48. The slider and return spring are shown in dotted outline in FIG. 32. A lever 42 operates the slider 46 through the linkage or transfer bar 44. The closure of the lever 42 pulls the cable 50 to close the jaws 52, 54. For further details of the tool actuation mechanism refer to co-pending application Ser. No. 11/185,911, filed on Jul. 20, 2005, the content of which is hereby incorporated by reference herein.

In FIG. 32 the guide member or guide instrument 10 is depicted separately from the surgical instrument 12. In FIG. 33, there is shown the assembled system with the instrument having been inserted into and through the lumen 58 of the guide member 10. In FIG. 33 note that the guide member shaft 18 extends through the cannula 8 at the insertion site 6 of the patient's skin 4. The end effector or tool 38 is disclosed in FIG. 33 as extending from the distal bendable member 22. FIG. 33 also shows a protective sheath 24 that may extend about the distal flex member 22.

The guide member 10, in addition to including the guide shaft 18, also includes the proximal flexible or bendable member 20 and the distal flexable or bendable member 22. An adaptor cover 26 is disposed about a portion of the proximal bendable member 20. The adaptor cover 26 includes a funnel or conical-shaped portion for receiving ends of the proximal bendable member 20 and the guide shaft 18. The rotation knob 294 of the guide member 10 receives the other end of the proximal bendable member 20. The rotation knob 294, as shown in FIGS. 35 and 36, interlocks with the hub or grip portion 292. The manual instrument 12 is illustrated as having an end boss 30 that is provided with a recess 32 for receiving a spring loaded latch 282 that extends into the recess 32 in the instrument boss 30. The use of the spring loaded latch 282 secures the instrument 12 within the guide member 10. The latch 282 is supported by the hub 292, as shown in FIG. 35. Motions of the instrument 12 are thus directly transferred to the hub 292 and, in turn, to the proximal bendable member 20. Thus, a user can insert the manual instrument in the guide member, and then control the distal part of the manual instrument by moving or deflecting the handle 40 such as to a position illustrated in FIG. 36. This occurs while the instrument control also is enabled via the rotation knob. The relative length of the guide member and instrument are selected so that the instrument tool extends beyond the end of the guide member, as depicted in FIG. 33.

In FIGS. 32-36 there is shown some details of the proximal and distal bendable members 20 and 22. Bendable member 20 has a central passage through which the instrument shaft 36 can extend. In this regard the lumen 58 defined in the guide shaft 18 maybe considered as extending also through both bendable members. Thus, the distal bendable member 22 also includes a passage for receiving the instrument shaft 36. The guide shaft 18 may be rigid, partially rigid or flexible. The guide shaft 18 may be made of a light weight metal material or of plastic.

The rotation knob 294 receives one end of the proximal bendable member 20. This bendable member 20 is seated at a center section of the rotation knob 294, as depicted in FIGS. 35 and 36. The rotation knob also receives the ends of cabling at anchors and possible associated springs. This includes a plurality of proximal anchors and related springs. The springs are for tensioning the associated cables 76-82. The distal bendable member 22 includes an extending end for receiving the distal anchors 84 that secure the distal ends of the actuation cables 76-82.

The control between the proximal and distal bendable members is carried out primarily by means of a set of cables that extend between these bendable members. A bending at the proximal bendable member causes a pulling of one or more cables while there is a relaxing of other opposed cables causing a corresponding bending action at the distal bendable member. The cabling that is used includes flexible cables 76, 78, 80 and 82 that extend between the proximal and distal bendable members. A plurality of distal anchors 84 are used at the distal end of the cabling. Cable passages are provided in the proximal bendable member 20, and cable passages are provided in the distal bendable member 22. The passages accommodate these cables. Also, guide discs (not shown) may be provided along the cables, particularly within the guide shaft 18 so assure that the cables are maintained in position as they extend from one end of the guide shaft to the other end.

The proximal bendable member 20 is comprised of a series of adjacent discs that define therebetween spaces or slots. Connecting ribs may extend between adjacent discs. In a similar manner, the distal bendable member 22 includes a series of discs that define therebetween slots or spaces. Ribs may extend between adjacent discs. For further details of the bendable members and the prefered relationship between the disks, slots and ribs, refer to application Ser. No. 11/185,911, filed on Jul. 20, 2005, the content of which is hereby incorporated by reference herein.

The angle locking and rotation means 290 allows the instrument user to hold a particular position and orientation of the guide member and, in turn, the instrument itself. The locking member comprises an angle locking means 290 that includes a ball and socket arrangement that is compressed by an outer cinch ring member. The locking mechanism or angle locking means 290 includes a ball and socket arrangement that is disposed over the proximal bendable member 20 and that follows the bending at the proximal bendable member.

The locking mechanism has locked and unlocked positions, is disposed about the proximal movable or bendable member and is manually controlled from the manually operated instrument 12 so as to fix the position of the proximal movable member relative to the handle 12 in the locked position thereof. The locking mechanism comprises a ball member and a compressible hub that defines a socket member. In the disclosed embodiment the hub is a split hub and the locking mechanism further includes a cinch ring disposed about the split hub and a locking lever mounted on the cinch ring for closing the cinch ring about the hub to lock the hub against the spherical ball member. The cinch ring interlocks with the hub but is preferably able to rotate relative thereto when in the unlocked position.

The "ball" part is basically formed by the ball member 252, while the "socket" part is basically formed by an extension of the handle, namely the split hub 264, and identified in the drawings by the socket 270. The locking mechanism locks the proximal bendable member in a desired position and by doing that also locks the position of the distal bendable member 22 of the guide and tool 38 of the manually operated instrument 10. The proximal bending member 20, although it is enclosed by the ball and socket arrangement, still allows the instrument shaft 18 and the proximal bending member 20, along with the cabling 76, 78, 80, 82, to rotate freely while also allowing the axis of the instrument shaft 36 to be angled relative to the axis of the handle in a free, or alternately, locked mode.

For this purpose refer to the ball member 252 which is shown in further detail in FIGS. 35 and 36. The ball member 252 includes a distal neck 254 that is contiguous with a partially spherical ball end having a partially spherical outer surface. The neck 254 is basically disposed over the adaptor 26 and conical portion 19 of the proximal bendable member 20, while the ball 252 portion is mainly disposed over the primary part of the proximal bendable member 20. The ball member 252 is adapted to sit within a socket 270 that is formed in the handle in the form of the split hub 264 that can be collapsed about the ball member 252 by radially compressing the cinch ring 266.

The ball member 252 is gimbaled in the split hub 264 that is comprised of four quadrants or petals 264A-264D that can be clamped against the outer spherical surface of the ball member 252 by means of the cinch ring 266. The split hub 264 is supported at the distal end of the handle by means of a plurality of spacedly disposed struts 272 that, in one embodiment, are spaced approximately 120 degrees apart. The struts are supported from the proximal hub 274, as shown in FIG. 35. As mentioned previously, the ball member 252 has a neck portion 254 that provides support for the distal end of the proximal bendable member 20. In this regard a bearing surface 256 is provided, as illustrated in FIGS. 35 and 36, between the proximal end of the neck 254 and the adaptor 26. This enables the proximal bendable member, along with the adaptor 26 to be free to rotate relative to the ball member 252. FIGS. 35 and 36 also illustrate a bearing surface at 258 between the very distal end of the neck 254 and the outer tube or shaft 18. These bearing surfaces 256, 258 may be formed by actual bearings at those locations.

FIGS. 32-36 illustrate the cinch ring 266. The cinch ring 266 is an annular member that may be provided with an internal ridge or spline that is adapted to mate with a channel or groove in the outer surface of the split hub. This combination of a channel and ridge limits the annular cinch member to just rotation about the hub. FIG. 34 shows that each of the portions 264A-264D of the split hub connects to the instrument handle via respective struts 272 (see also FIG. 35). When the cinch ring 266 is closed this, in turn, closes the slotted hub and essentially compresses the socket 270 against the outer spherical surface of the ball member 252. The locking of the ball member thus fixes the position of the proximal bendable member 20, and, in turn, the distal bendable member 22 and tool 38. For further details of the ball and socket arrangement and associated cinch ring construction refer to co-pending application Ser. No. 11/649,352 filed on Jan. 2, 2007, the entire contents of which is hereby incorporated by reference.

The cinch ring 266 is operated by means of an over-center locking lever 268 that is connected to ends of the cinch ring 266 by means of the pins or the like. FIG. 28 illustrates the lock lever 268 in a locked position while FIG. 29 illustrates the lock lever in a released or unlocked position. The cinch ring 266 is free to rotate around the split hub when lever 268 is released by means of the spline that rides in the groove in the circumference of the split hub. This allows for left or right handed operation of the instrument.

When the locking lever 268 is moved to its locked position this compresses the cinch ring 266 closing the hub against the spherical outer surface of the ball member 252. This locks the hub 274 against the ball member 252 holding the ball member in whatever position it is in when the locking occurs. By holding the ball member in a fixed position this, likewise, holds the proximal bendable member in a particular position and fixed in that position. This, in turn, maintains the distal bendable member and tool at a fixed position, but the instrument orientation can be controlled via the control of the rotation knob 294 which controls the orientation of the instrument tip by enabling rotation of the distal bendable member and tool about the tip axis P (see FIG. 33).

In the embodiment of FIGS. 32-36 because the handle is locked with the guide member by means of the latch 282, when the handle is rotated in the direction of the arrow R10 then the end effector 38 actually orbits in and out of the plane of the paper in FIG. 33. The rotation of the handle provides rotation of the guide shaft, as well as the instrument shaft, but this is transferred to the tip of the instrument by orbiting the end effector. In the position shown in FIG. 33, if the rotation knob 294 is operated, such as indicated by the rotational arrow R20, then the end tool 38 rotates about the distal tool axis represented in FIG. 33 by the tool axis P. This is illustrated in FIG. 33 by the distal rotation arrow R21. If the latch 282 is constructed so that it is releasable, then the manual instrument may be rotated separately from the guide member. In that case, if the guide member is held stationary (but in a bent condition, for example, per FIG. 33) when the manual instrument is rotated, such as in the direction of arrow R10 in FIG. 33, then the end tool 38 rotates about the distal tool axis represented in FIG. 33 by the axis P.

Figure 39:
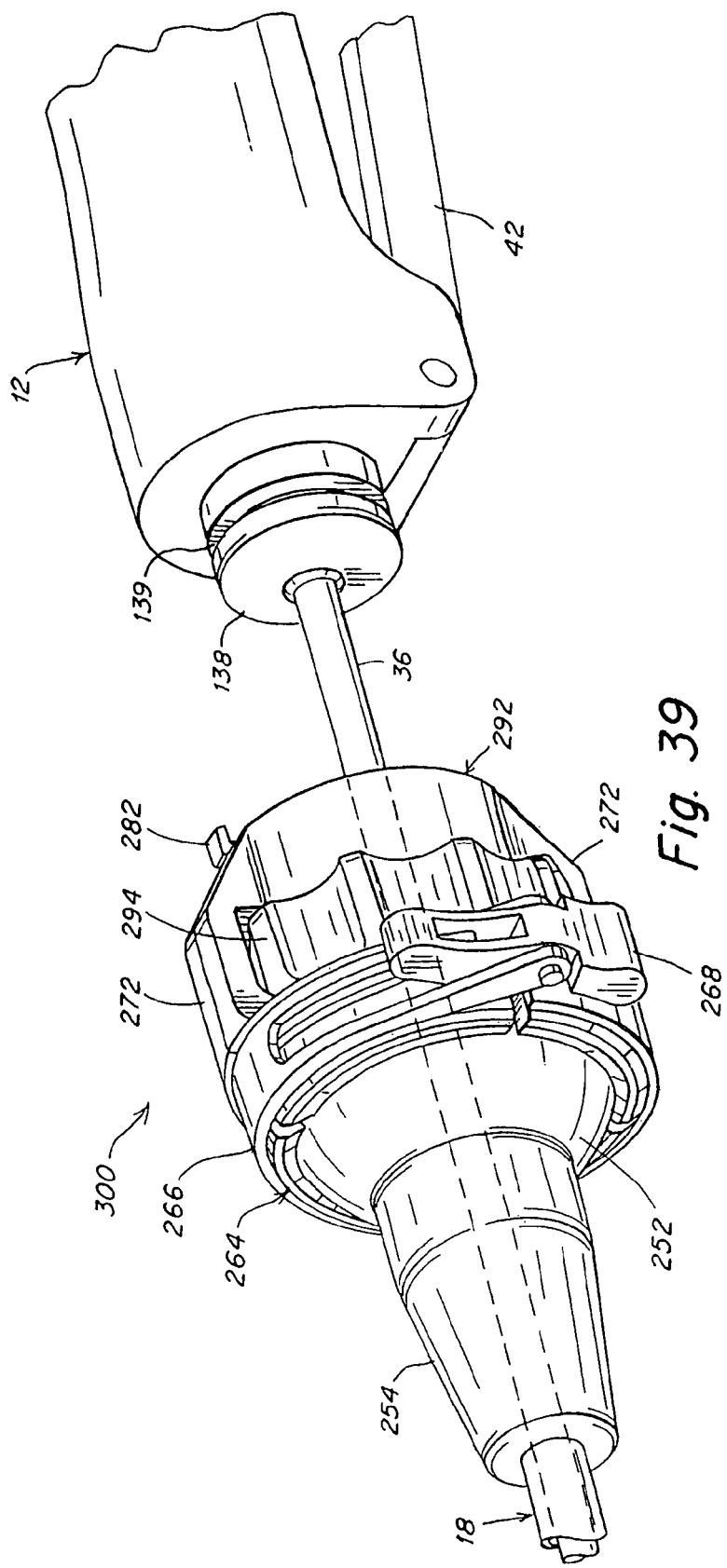
FIG. 39 is a partially exploded perspective view of the manually operated instrument being inserted into the guide member.

In the embodiment of FIG. 26, as well as the embodiment of FIG. 32 the handle is fixed with the guide member, such as with the latch that is illustrated. On the other hand in the next embodiment that is illustrated in FIGS. 37-39 there is provided relative rotation between the handle 40 and the guide member 10. For this purpose, rather than fixing the position of the guide member relative to the handle, the handle is provided with a boss 138 that includes a peripheral groove or channel 139 that receives the distal end of the latch 282. The boss 138 fits within the cavity 296 in the grip portion 292. This arrangement allows the relative movement between the handle and guide member by virtue of the latch having the capability of rotating about the boss 138 in the groove 139. This essentially provides an extra degree of freedom for the instrument system.

Other than the configuration of the boss in this embodiment, all of the other elements of both the guide member and manual instrument are the same as previously described in connection with the embodiment shown in FIGS. 32-36. This includes such elements as the rotation knob 294, the angle locking means 300, cinch ring 266 and support struts 272. Refer to the previous description of FIGS. 26-36 for further details of, inter alia, the angle locking means and rotation knob. Thus, the entire manually operated instrument 12 can be rotated relative to the guide member 10, and furthermore, the rotation knob 294 can be used independently to rotate the manual instrument tip about its distal tip axis P. Note in FIG. 38 the rotational arrows R10, R20 and R21.

Figure 42:
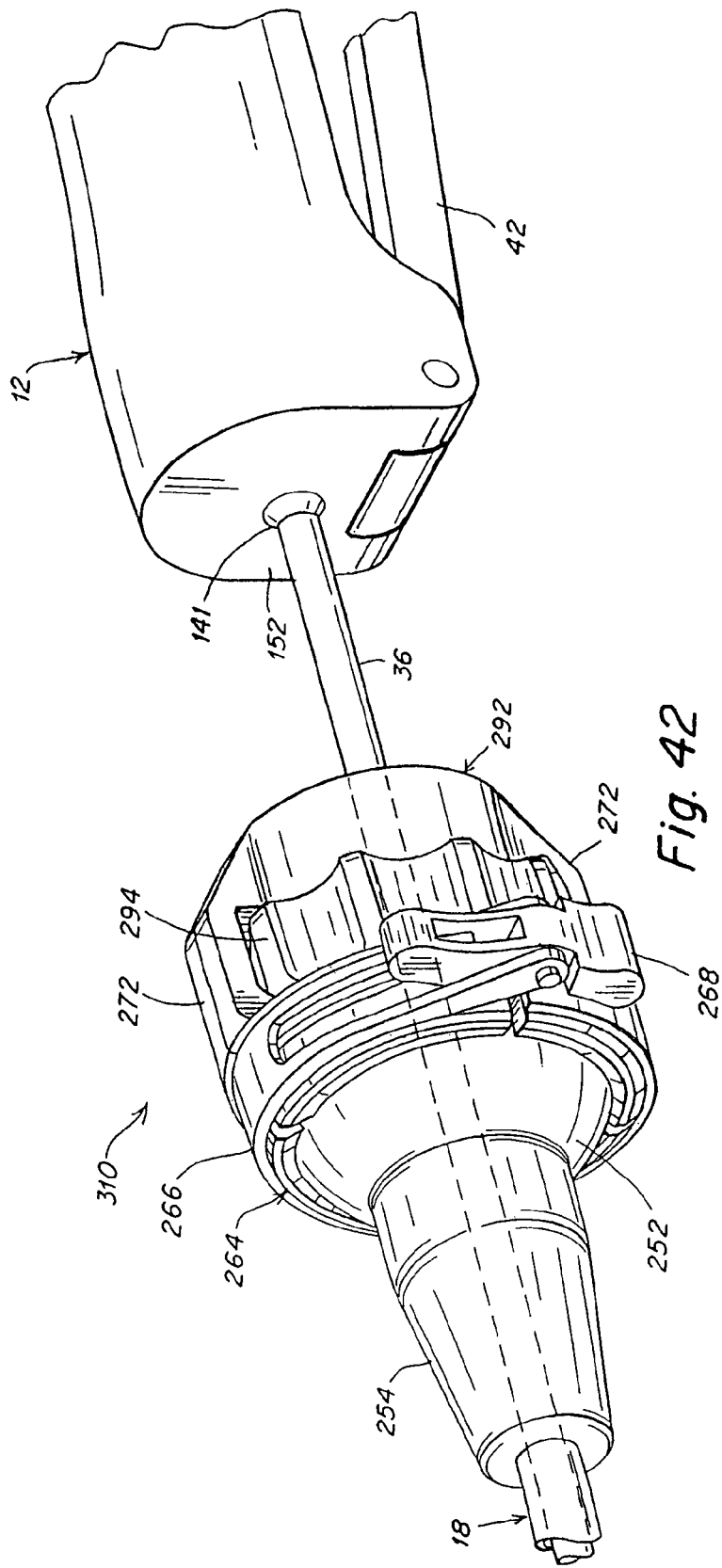
FIG. 42 is a partially exploded perspective view of the manually operated instrument being inserted into the guide member.

Reference is now made to a last embodiment of the present invention shown in FIGS. 40-42. As with the previous embodiments described in FIGS. 26-39, the same elements are used for about all of the instrument system. This thus includes a manually operated instrument 12 that is received in the guide member 10. This embodiment also includes an angle locking means 310 that is substantially the same as previously described angle locking means. The primary difference between this embodiment and previously described embodiments is that the manual instrument 12 is not fixed with the guide member 10. Instead, the manually operated instrument 12 is allowed to move linearly relative to the guide member 10. FIG. 40 shows an exploded side view of the manual instrument and guide member and including a locking feature. FIG. 41 is a schematic side view of the instrument of FIG. 40 and in use. FIG. 42 is a partially exploded perspective view of the manually operated instrument being inserted into the guide member.

In the embodiment illustrated in FIGS. 41-42 the manually operated instrument shaft 36 is insertable in the internal lumen 58 of the guide member 10 and may be controlled by inserting or withdrawing the manually operated instrument 12. When fully inserted the proximal end 141 of the instrument shaft 36 engages with the tapered cavity 314 in the end wall 312 of the grip portion 292, as shown in FIG. 40. In FIG. 41 the linear motion of the manually operated instrument 12 is illustrated by the proximal arrow 145 and the corresponding distal arrow 147. Also rotation or pivoting of the instrument handle indicated by the arrow 151 (R10) in FIG. 41 causes a corresponding rotation or pivoting of the end effector 38 as illustrated by the arrow 157. In FIG. 41, arrow 151 indicates a bending at the proximal bendable member 20 and arrow 153 indicates a corresponding bending at the distal bendable member 22. Arrow R10 indicates rotation of the handle alone while arrow R21 shows the corresponding rotation at the tool 38. Rotation of the knob 294 (arrow R20) also causes rotation of the tool.

Having now described one embodiment of the present invention, it should now be apparent to those skilled in the art that numerous other embodiments and modifications thereof are contemplated as falling within the scope of the present invention as defined by the appended claims. For example, the guide member that is described herein, in particular in FIGS. 26-42, where there is the locking feature, can also be applied to the earlier version of FIG. 24 where the guide member can receive multiple manual instruments. Any one of the different embodiments of FIGS. 26-42 can be applied to the multiple channel guide tube of FIG. 24. Depending on whether the manual instrument is locked with the guide or not different control aspects can be provided. For example, a control at the guide member of that rotation knob can control rotation of the distal end of the guide, while rotation of the individual instrument rotation knobs provides individual rotational control of the respective tools.

What is claimed is:

1. A guide device for controlling a manually operated medical instrument that includes at least
a handle, instrument shaft and distal tool, said guide device comprising:
an elongated guide shaft having proximal and distal ends and including an instrument lumen for receiving therethrough the manually operated medical instrument;
a distal bendable member disposed at the distal end of the elongated guide shaft;
a proximal bendable member disposed at the proximal end of the elongated guide shaft;
actuation means extending between said distal and proximal bendable members and providing a bending of said distal bendable member controlled from said proximal bendable member;
said proximal bendable member being controlled from said manually operated medical instrument to cause a corresponding bending of said distal bendable member and control of said distal tool;
and a locking mechanism for fixing the position of the distal tool at a selected position and having locked and unlocked states;
said locking mechanism including a ball and socket arrangement disposed about said proximal motion member and a cinch member for locking said ball and socket arrangement.

2. The guide device of claim 1 wherein said actuation means is constructed and arranged so that a bending of the proximal bendable member causes a like direction bending of the distal bendable member.

3. The guide device of claim 1 wherein said actuation means is constructed and arranged so that a bending of the proximal bendable member causes an opposite direction bending of the distal bendable member.

4. The guide device of claim 1 wherein said proximal bendable member is moveable in any direction.

5. The guide device of claim 1 including a grip disposed between said proximal bendable member and the handle of said manually operated medical instrument and constructed and arranged to have a passage through which the manually operated medical instrument shaft extends.

6. The guide device of claim 5 wherein said grip is formed as two pieces including a grip portion and a rotation knob and said grip and knob portions are supported for relative rotation therebetween.

7. The guide device of claim 5 including means or securing the manually operated medical instrument handle to the grip portion.

8. The guide device of claim 1 wherein said bendable members each comprise a unitary slotted structure having a plurality of discs separated by slots.

9. The guide device of claim 1 wherein the ball and socket arrangement comprises a grip portion and a ball member having a partially spherical portion that mates with a concave socket in the grip portion.

10. The guide device of claim 9 wherein said grip portion has the socket formed therein and said cinch member includes an annular cinch ring that is disposed about said grip portion.

11. The guide device of claim 10 including a tongue and groove interconnection between said cinch ring and grip portion so as to permit rotation therebetween while preventing axial movement.

12. The guide device of claim 11 including a locking lever on said cinch ring having opposed locked and unlocked positions.

13. The guide device of claim 12 wherein said grip portion includes a split hub that is compressable by the cinch ring as the cinch ring is locked via the locking lever.

14. The guide device of claim 1 wherein said guide device is rotational relative to the manually operated medical instrument.

15. The guide device of claim 1 wherein said manually operated medical instrument is slideable linearly relative to said guide device.

16. A guide device for controlling a manual instrument that has a handle instrument shaft and distal tool, comprising, a proximal control handle, a guide shaft and proximal and distal bendable members that respectively intercouple said proximal and distal bendable members, cable actuation means disposed between said bendable members, for controlling the positioning of said distal tool, and a locking mechanism having locked and unlocked positions, said locking mechanism including a ball and socket arrangement disposed about said proximal motion member and a cinch member for locking said ball and socket arrangement.

17. The guide device of claim 16 wherein said locking mechanism comprises a ball member and a compressible hub that defines a socket member.

18. The guide device of claim 17 wherein said hub is a split hub and said locking mechanism further includes a cinch ring disposed about said split hub and a locking lever mounted on said cinch ring for closing said cinch ring about said hub to lock said hub against said ball member.

19. The guide device of claim 18 wherein said cinch ring interlocks with said hub but is able to rotate relative thereto when in the unlocked position.

20. The guide device of claim 16 including a hub and a rotation knob supported by said hub.

* * * * *